(12) United States Patent
Hansen

(10) Patent No.: US 9,616,120 B2
(45) Date of Patent: Apr. 11, 2017

(54) MONOCLONAL ANTIBODIES DIRECTED TO CD20

(75) Inventor: Genevieve Hansen, Del Mar, CA (US)

(73) Assignee: VET THERAPEUTICS, INC., Del Mar, CA (US)

( * ) Notice: Subject to any disclaimer, the term of this patent is extended or adjusted under 35 U.S.C. 154(b) by 350 days.

(21) Appl. No.: 13/048,135

(22) Filed: Mar. 15, 2011

(65) Prior Publication Data

US 2011/0217298 A1 Sep. 8, 2011

Related U.S. Application Data

(63) Continuation of application No. PCT/US2011/000415, filed on Mar. 4, 2011.

(60) Provisional application No. 61/310,440, filed on Mar. 4, 2010.

(51) Int. Cl.
| | | |
|---|---|---|
| C07K 16/28 | (2006.01) | |
| A61K 39/395 | (2006.01) | |
| C07H 21/00 | (2006.01) | |

(52) U.S. Cl.
CPC ........... *A61K 39/395* (2013.01); *C07H 21/00* (2013.01); *C07K 16/28* (2013.01); *C07K 16/2887* (2013.01); *C07K 2316/52* (2013.01)

(58) Field of Classification Search
None
See application file for complete search history.

(56) References Cited

U.S. PATENT DOCUMENTS

| | | | |
|---|---|---|---|
| 5,225,539 A | 7/1993 | Winter | |
| 5,760,185 A | 6/1998 | Kimachi et al. | |
| 5,852,183 A | 12/1998 | Maeda et al. | |
| 6,028,059 A | 2/2000 | Curiel | |
| 6,468,738 B1 | 10/2002 | Kang et al. | |
| 6,703,360 B2 | 3/2004 | McCall et al. | |
| 7,117,096 B2 | 10/2006 | Luo et al. | |
| 7,342,110 B2 | 3/2008 | Hoffee et al. | |
| 7,393,648 B2 | 7/2008 | Rother et al. | |
| 7,531,628 B2 | 5/2009 | Beall | |
| 8,337,842 B2 | 12/2012 | Hansen | |
| 8,569,460 B2 | 10/2013 | Hansen | |
| 8,652,470 B2 | 2/2014 | Hansen | |
| 2002/0041847 A1 | 4/2002 | Goldenberg | |
| 2002/0165135 A1 | 11/2002 | McCall et al. | |
| 2003/0219433 A1* | 11/2003 | Hansen et al. | 424/141.1 |
| 2003/0219861 A1 | 11/2003 | Rother et al. | |
| 2004/0181039 A1 | 9/2004 | Krah et al. | |
| 2005/0271662 A1* | 12/2005 | Beall | 424/144.1 |
| 2006/0040325 A1 | 2/2006 | Wu et al. | |
| 2006/0134709 A1 | 6/2006 | Stavenhagen | |
| 2006/0183195 A1 | 8/2006 | Longberg et al. | |
| 2007/0004909 A1 | 1/2007 | Johnson | |
| 2007/0020259 A1 | 1/2007 | Hansen et al. | |
| 2007/0036799 A1 | 2/2007 | Stavenhagen et al. | |
| 2007/0141047 A1 | 6/2007 | McCall et al. | |
| 2008/0050370 A1 | 2/2008 | Glaser et al. | |
| 2008/0112961 A1 | 5/2008 | Stavenhagen et al. | |
| 2008/0188401 A1 | 8/2008 | Cruwys | |
| 2008/0248529 A1 | 10/2008 | Carr et al. | |
| 2008/0299546 A1 | 12/2008 | Kano | |
| 2010/0061988 A1 | 3/2010 | Hansen | |
| 2011/0002917 A1 | 1/2011 | Hansen | |
| 2011/0217304 A1 | 9/2011 | Hansen | |
| 2013/0071385 A1 | 3/2013 | Hansen | |
| 2013/0344077 A1 | 12/2013 | Hansen | |
| 2014/0234297 A1 | 8/2014 | Hansen | |
| 2014/0341912 A1 | 11/2014 | Hansen | |

FOREIGN PATENT DOCUMENTS

| | | |
|---|---|---|
| EP | 0419858 A1 | 4/1991 |
| WO | WO 0194585 A1 | 12/2001 |
| WO | WO 03048208 A2 | 6/2003 |
| WO | WO 03060080 A2 | 7/2003 |
| WO | WO 03068821 A2 | 8/2003 |
| WO | WO 03072736 A2 | 9/2003 |
| WO | WO 2004003019 A2 | 1/2004 |
| WO | WO 2005075640 A1 | 8/2005 |
| WO | WO 2006/126068 | 11/2006 |
| WO | WO 2006126068 A2 | 11/2006 |
| WO | WO 2010027488 A2 | 3/2010 |
| WO | WO 2010110838 A2 | 9/2010 |
| WO | WO 2011109662 A1 | 9/2011 |

OTHER PUBLICATIONS

MacCallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Chun, "Lymphoma: Which Chemotherapy Protocol and Why?" Topics in Companion Animal Medicine, 24 (3): 157-162 (2009).
Gershwin, L., "Veterinary Autoimmunity: Autoimmune Diseases in Domestic Animals", Ann. N.Y. Acad Sci. 1109: 109-116 (2007).
Jubala, C.M., et al., "CD20 Expression in Normal Canine B Cells and in Canine non-Hodgkin Lymphoma" Vet. Pathol. 42: 468-476 (2005).
Kano et al., "Canine CD20 gene" Vet. Imm. Immunopath. 108: 265-268 (2005).
Mirzabekov et al., "Paramagnetic proteoliposomes containing a pure, native, and oriented seven-transmembrane segment protein, CCR5" Nat. Biotech. 18: 649-654 (2000).
Tang et al., "Cloning and characterization of cDNAs encoding four different canine immunoglobulin gamma chains" Vet. Imm. Immunopath. 80: 259-270 (2001).
Wilkerson et al., "Lineage differentiation of canine lymphoma/leukemia's and aberrant expression of CD molecules" Vet. Imm. and Immunopath. 106 (3-4): 179-96 (2005).

(Continued)

*Primary Examiner* — Ronald Schwadron
(74) *Attorney, Agent, or Firm* — Hoxie & Associates LLC

(57) ABSTRACT

The invention provides antibody to canine or feline or equine antigens. Specifically, antibodies directed to canine CD20 which have been caninized or felinized are provided. Also provided are methods for preparing high affinity antibodies to canine and feline CD20 as well as methods for treating B cell disorders in companion animals.

11 Claims, No Drawings

(56) References Cited

OTHER PUBLICATIONS

Adamski, King and Demmer, "Expression of the Fc receptor in the mammary gland during lactation in the marsupial Trichosurus vulpecula (*brushtail possum*)", Mol Immunol 37: 435-444 (2000).

Babcock, et al. "Ligand Binding Characteristics of CXCR4 Incorporated into Paramagnetic Proteoliposomes" ; The Journal of Biological Chemistry; 276 (42): 3843-38440 (2001).

Carter et al., "Canine rheumatoid arthritis and inflammatory cytokines" Vet. Immun. Immunopath. 69: 201-214 (1999).

Casset et al., "A Peptide Mimetic of an anti-CD4 Monoclonal Antibody by Rational Design" BBRC [2003] 307: 198-205).

Chaudhury, Mehnaz, Robinson, Hayton, Pearl and Roopenian. et al., "The major histocompatibility complex-related Fc receptor for IgG (FcRn) binds albumin and prolongs its lifespan", The Journal of Experimental Medicine 197: 315-322 (2003).

Chen et al., "Selection and Analysis of an Optimized Anti-VEGF Antibody: Crystal Structure of an Affinity-matured Fab in complex with Antigen", (J. Mol. Bio. [1999] 293, 865-881).

Cianga, Medesan, Richardson, Ghetie and Ward, "Identification and function of neonatal Fc receptor in mammary gland of lactating mice," Eur J Immunol 29: 2515-2523 (1999).

Das, et al. "Evolutionary Dynamics of the Immunoglobulin Heavy Chain Variable Region Genes in Vertebrates", Immunogenetics, 60: 47-55 (2008).

Das, et al. "Evolutionary Redefinition of Immunoglobulin Light Chain Isotypes in Tenapods Using Molecular Markers", Proc. Nat'l Acad. Sci. 105(43): 16647-16652 (2008).

Davis, et al. (An extended family of Fc receptor relatives. Eur J Immunol (2005) 35: 674-680.

Day et al.; "Tissue Immunoglobulin G Subclasses Observed in Immune-mediated Dermatopathy, Deep Pyoderma and Huypersensitivity Dermatitis in Dogs"; Vet. Sci. 58: 82-89 (1995).

Doom et al., "Immunopathological mechanisms in dogs with rupture of the cranial cruciate ligament" 125: 143-161 (2008).

Fayngerts, et al. "Species-specific Evolution of the FcR Family in Endothermic Vertebrates", Immunogenetics 59: 493-506 (2007).

Ghetie and Ward, "Multiple roles for the major histocompatibility complex class I- related receptor FcRn",Annu Rev Immunol 18: 739-766 (2000).

Hale et al., "CD52 (CAMPATH-1)" J Biol Regul Homeost Agents 15: 386-91 (2001).

Helfand, Hank, Gan and Sondel. Lysis of Human Tumor Cell Lines by Canine Complement plus Monoclonal Antiganglioside Antibodies or Natural Canine Xenoantibodies. Cellular Immunology 167: 99-107 (1996).

Jang et al., "The structural basis for DNA binding by an anti-DNA autoantibody", (Molec. Immunol. [1998] 35: 1207-1217).

Kacskovics, Wu, Simister, Frenyo and Hammarstrom, Cloning and characterization of the bovine MHC class I-like Fc receptor, J Immunol 164: 1889-1897 (2000).

Kobayashi et al., "Trytophan H33 plays an important role in pyrimidine (6-4) pyrimidine photoproduct binding by a high-affinity antibody" (Protein Engineering [1999] 12: 879-844).

Lilliehöok, Johannisson, and Hakansson. Expression of adhesion and Fcgamma-receptors on canine blood eosinophils and neutrophils studied by anti-human monoclonal antibodies. Vet Immunol Immunopathol. 61: 181-93 (1998).

Maccoux, L.J., et al. "Expression profiling of select cytokines in canine osteoarthritis tissues" Vet. Immun. Immunopath. 118: 59-67 (2007).

Maltais Lovering, Taranin, Colonna, Ravetch, Dalla-Favera, Burrows, Cooper, Davis New nomenclature for Fc receptor-like molecules. Nat Immunol 7: 431-432 (2006).

Mayer et al., Expression of the neonatal Fc receptor (FcRn) in the bovine mammary gland,J Dairy Res 72 (Spec No. 107-112) (2005).

Mayer, et al., Redistribution of the sheep neonatal Fc receptor in the mammary gland around the time of parturition in ewes and its localization in the small intestine of neonatal lambs, Immunology 107: 288-296 (2002).

Mazza et al. "The Separation and Identification by Monoclonal Antibodies of Dog IgG Fractions", J. Imm. Meth. 161: 193-203 (1993).

Mazza, et al. "Tissue Immunoglobulin G Subclasses Observed in Immune-mediated Dermatopathy, Deep Pyoderma and Hypersensitivity Dermatitis in Dogs", Vet. Sci. 58: 82-89 (1995).

Phillips et al. Immunostimulatory effects of human recombinant interleukin-12 on peripheral blood mononuclear cells from normal dogs. Vet Immunopathol. 70: 189-201 (1999).

Ravetch and Kinet "Fc Receptors." Annu Rev Immunol 9: 457-492 (1991).

Robinson et al.; "Albumin Turnover: FcRn-mediated Recycling Saves as Much Albumin for Degradation as the Liver Produces"; Am J Physiol Gastrointest Liver Physiol (2005).

Rodewald, R, pH-dependent binding of immunoglobulins to intestinal cells of the neonatal rat, J Cell Biol. 71: 666-669 (1976).

Sato, Teshima, Nakamura, Takagi, Sasaki, Sawada, and Kitani Canine mast cell activation via human IgG1 and IgG4. Int Arch Allergy Immunol. 135:154-60 (2004).

Schnulle and Hurley, Sequence and expression of the FcRn in the porcine mammary gland, Vet Immunol Immunopathol. (2003) 91: 227-231.

Shin et al., "Studies of cocktail therapy with multiple cytokines for neoplasia or infectious disease of the dog I. cDNA cloning of canine IL-3 and IL-6", J. Vet. Sci. 2 (2): 115-120 (2001).

Simister and Mostov an Fc receptor structurally related to MHC class I antigens, Nature 337: 184-187 (1989).

Smith-Gill et al., "Contributions of immunoglobulin heavy and light chains to antibody specificity for lysozyme and two haptens", (J. Immunol. [1987] 139: 4135-4144).

Song et al., "Light Chain of Natural Antibody Plays a Dominant Role in Protein Antigen Binding", (Biochem. Biophys. Res. Comm. [2000] 268: 390-394).

Sutton, et al., "The contribution of synovium, synovial derived inflammatory cytokines and neuropeptides to the pathogenesis of osteoarthritis", Vet. J. 179: 10-24 (2009).

Vajdos et al., "Comprehensive Functional Maps of the Antigenbinding Site of an Anti-ErbB2 Antibody Obtained with Shotgun Scanning Mutagenesis", (J. Mol. Biol. [2002] 320, 415-428).

Ward et al., "Binding activities of a repertoire of single immunoglobulin variable domains secreted from *Escherichia coli*", (Nature [1989] 341: 544-546).

Withrow & MacEwen's, "Small Animal Clinical Oncology" (Ed. 4)), D. Vail and S. Withrow, Ed.s, Saunders Elsevier, St Louis, (2007); Title Page.

Wozna, et al., "The immunological. biochemical and molecular bases of canine senescence and carcinogenesis: a review", Veterinami Medicina, 57 (7): 350-359 (2012.

Wu et al., "Humanization of a Murine Monoclonal Antibody by Simultaneous Optimization of Framework and CDR Residues", (J. Mol. Biol. [1999] 294, 151-162).

Gong, R., et al., "Engineered Human Antibody Constant Domains with Increased Stability", The Journal of Biological Chemistry, vol. 284, No. 21, pp. 14203-14210, (May 22, 2009).

Holm et al., "Functional Mapping and Single Chain Construction of the Anti-Cytokeratin 8 Monoclonal Antibody TS1", (Mol. Immunol. [2007] 44: 1075-1084).

Brorson, K. et al., "Mutational Analysis of Avidity and Fine Specificity of Anti-Levan Anti-bodies", The Journal of Immunology, vol. 163, pp. 6694-6701, http://www.jimmunol.org/content/163/12/6694, (1999).

Brummell, D.A., et al., "Probing the Combining Site of an Anti-Carbohydrate Antibody by Saturation-Mutagenesis: Role of Heavy-Chain CDR3 Residues", Biochemistry, vol. 32, No. 4, pp. 1180-1187, (1993).

Burks, E. A. et al., "In Vitro Scanning Saturation Mutagenesis of an Antibody Binding Pocket", Proc. Natl. Acad. Sci. USA, vol. 94, pp. 412-417, (Jan. 1997).

Caldas, C., et al., "Humanization of the Anti-CD18 Antibody 6.7: An Unexpected Effect of a Framework Residue in Binding to Antigen", Molecular Immunology, vol. 39, pp. 941-952, (2003).

Chien, N.C., et al., "Significant Structural and Functional Change of an Antigen-Binding Site by a Distant Amino Acid Substitution:

(56) References Cited

OTHER PUBLICATIONS

Proposal of a Structural Mechanism", Proc. Natl. Acad. Sci. USA, vol. 86, pp. 5532-5536, (Jul. 1989).
Cianga, P., et al, "The MHC Class I Related Fc Receptor, FcRn, is Expressed in the Epithelial Cells of the Human Mammary Gland", Human Immunology, vol. 64, pp. 1152-1159, doi:10.1016/j.humimm.2003.08.025, (2003).
Colman, P.M., "Effects of Amino Acid Sequence Changes on Antibody-Antigen Interactions", Research in Immunology, vol. 145, pp. 33-36, (Jan. 1994).
Daeron, M., "Fc Receptor Biology", Annu. Rev. Immmuol., vol. 15, pp. 203-234, (1997).
Day, M.J., et al., "Tissue Immunoglobulin G Subclasses Observed in Immune-Mediated Dermatopathy, Deep Pyoderma and Hypersensitivity Dermatitis in Dogs", Research in Veterinary Science, vol. 58, pp. 82-89, (1995).
De Pascalis, R., et al., "Grafting of "Abbreviated" Complementarity—Determining Regions Containing Specificity-Determining Resides Essential for Ligand Contact to Engineer a Less Immunogenic Humanized Monoclonal Antibody", The Journal of Immunology, J. Immunol., vol. 169, pp. 3076-3084, http://www.jimmunol.org/content/169/6/3076, (2002).
Dutra, A.P., et al., "c-erbB-2 Expression and Nuclear Pleomorphism in Canine Mammary Tumors", Brazilian Journal of Medical and Biological Research, vol. 37, No. 11 pp. 1673-1681, (2004).
Extended European Search Report Issued on Dec. 21, 2012 for EP Application EP09811845.8 (EP entry date: Mar. 8, 2011, Title of Application: Monoclonal Antibodies, Inventor: Genevieve Hansen, Applicant: Vet Therapeutics, Inc.).
Extended European Search Report Issued on Jun. 5, 2013 for EP Application EP10756449.4 (EP entry date: Oct. 11, 2011, Title of Application: Antibody Constant Domain Regions and Uses Thereof, Inventor: Genevieve Hansen, Applicant: Vet Therapeutics, Inc.).
Extended European Search Report Issued on Jul. 10, 2013 for EP Application EP11751388.7 (EP entry date: Oct. 3, 2012, Title of Application: Monoclonal Antibodies Directed to CD52, Inventor: Genevieve Hansen, Applicant: Vet Therapeutics, Inc.).
Giusti, A.M., et al., "Somatic Diversification of S107 from an Antiphosphocholine to an anti-DNA Autoantibody is Due to a Single Base Change in its Heavy Chain Variable Region", Proc. Natl. Acad. Sci. USA, vol. 84, pp. 2926-2930, (May 1987).
Gussow, D., et al., "Humanization of Monoclonal Antibodies", Methods in Enzymology, vol. 203, pp. 91-121, (1991).
Holm, P., et al., "Functional Mapping and Single Chain Construction of the Anti-Cytokeratin 8 Monoclonal Antibody TS1", Mol. Immunol., vol. 44, pp. 1075-1084, (2007).
International Search Report and Written Opinion of the ISA/US Issued on Apr. 2, 2012 for International Application PCT/US2010/000666 (Int. Filing Date: Mar. 4, 2010, Title of Application: Antibody Constant Domain Regions and Uses Thereof, Inventor: Genevieve Hansen, Applicant: Vet Therapeutics, Inc.).
International Search Report and Written Opinion of the ISA/US Issued on May 4, 2011 for International Application PCT/US2011/027094 (Int. Filing Date: Mar. 3, 2011, Title of Application: Monoclonal Antibodies Directed to CD52, Inventor: Genevieve Hansen, Applicant: Vet Therapeutics, Inc.).
Kim, J, et al., "Albumin Turnover: FcRn-Mediated Recycling Saves as Much Albumin from Degradation as the Liver Produces", Am. J. Physiol. Gastrointest. Liver Physiol., vol. 290, pp. G352-G360, doi:10.1152/ajpgi.00286.2005, (Oct. 6, 2005).
Mariuzza, R.A., et al., "The Structural Basis of Antigen-Antibody Recognition", Ann. Rev. Biophys. Biophys. Chem. vol. 16, pp. 139-159, (1987).
Mayer, B., et al., "Localization of the Sheep FcRn in the Mammary Gland", Veterinary Immunology and Immunopathology, vol. 87, pp. 327-330, (2002).
R&D Systems product literature for antibody MAB16091 (Monoclonal Anti-canine IL-6 Antibody), http://www.rndsystems.com/pdf/MAB16091.pdf, accessed Apr. 3, 2014.
Rudikoff, S., et al., "Single Amino Acid Substitution Altering Antigen-Binding Specificity", Proc. Natl. Acad. Sci. USA, vol. 79, pp. 1979-1983, (Mar. 1982).
Soergel, S.A., et al., "The Immunotherapeutic Potential of Activated Canine Alveolar Macrophages and Antitumor Monoclonal Antibodies in Metastatic Canine Melanoma", J. Immunother., vol. 22, pp. 443-453 (1999).
Winkler, K., et al., "Changing the Antigen Binding Specificity by Single Point Mutations of an Anti-p24 (HIV-1) Antibody", J. Immunol , vol. 165, No. 8, pp. 4505-4514, (2000).
Written Opinion completed on Jan. 5, 2010 and mailed Feb. 17, 2010 for International Application No. PCT/US2009/004997, (International Application Filing Date: Sep. 4, 2009, Title of Application: Monoclonal Antibodies, Inventor: Genevieve Hansen, Applicant: Vet Therapeutics, Inc.).
Aratana Therapeutics, Inc., Press Release: "Aratana Therapeutics Provides Product Updates", Sep. 24, 2015, Kansas City, Kansas, PRNewswire, [online], [retrieved on May 17, 2016]. Retrieved from the Internet: <URL: http://aratana.investorroom.com/2015-09-24-Aratana-Therapeutics-Provides-Product-Updates>.
Aratana Therapeutics, Inc., Press Release: "Aratana Therapeutics Provides Update on Monoclonal Antibody Products", Jul. 22, 2015, Kansas City, Kansas, PRNewswire, [online], [retrieved on May 17, 2016]. Retrieved from the Internet: <URL: http://aratana.investorroom.com/2015-07-22-Aratana-Therapeutics-Provides-Update-on-Monoclonal-Antibody-Products>.
Aratana Therapeutics, Inc., Press Release: "Aratana Therapeutics Provides Product Updates: Provides additional details on AT-001 pivotal efficacy study, announces two technical section complete letters for safety, provides manufacturing update for AT-004, and announces completion of enrollment for AT-005's T-CHOMP study", Feb. 10, 2015, Kansas City, Kansas, PRNewswire, [online], [retrieved on May 17, 2016]. Retrieved from the Internet: <URL: http://aratana.investorroom.com/2015-02-10-Aratana-Therapeutics-Provides-Product-Updates>.
Aratana Therapeutics, Inc., Press Release: "Aratana Therapeutics Granted Full License for AT-004 by USDA: Represents a Novel Approach to Treating B-cell Lymphoma in Dogs", Jan. 5, 2015, Kansas City, Kansas, PRNewswire, [online], [retrieved on May 17, 2016]. Retrieved from the Internet: <URL: http://aratana.investorroom.com/2015-01-05-Aratana-Therapeutics-Granted-Full-License-for-AT-004-by-USDA>.
Beckman, "Antibody Constructs in Cancer Therapy", American Cancer Society, vol. 109, 2007, pp. 170-179.
Cespedes, "Mouse Models in Oncogenesis and Cancer Therapy", Clin Transl Oncol, vol. 8, No. 5, 2006, pp. 318-329.
Chabanne, L., "Immune-Mediated Hemolytic Anemia in the Dog", J. Clinical Immunology, World Congress, WSAVA/FECASAWA/CSAWA, 2006, pp. 456-459, [online], [retrieved on May 17, 2016]. Retrieved from the Internet: <URL: http://www.2ndchance.info/anemia-Chabanne2006ImmuneMediated.pdf>.
Davis, R.S., et al., "Fc Receptor Homologs: Newest Members of a Remarkably Diverse Fc Receptor Gene Family", Immunol. Rev., vol. 190, Dec. 2002, pp. 123-136, Abstract, [online], [retrieved on Nov. 13, 2012]. Retrieved from the Internet: <URL: http://www.ncbi.nlm.nih.gov/pubmed/12493010)>.
De Maria et al., "Spontaneous Feline Mammary Carcinoma IS a Model of HER2 Overexpressing Poor Prognosis Human Breast Cancer", Cancer Res., vol. 65, No. 3, Feb. 2005, pp. 907-912.
Dennis, "Off by a Whisker" Cancer News Feature, Nature Publishing Group, vol. 442, 2006, pp. 739-741.
Dufner, "Harnessing Phage and Ribosome Display for Antibody Optimisation" Trends in Biotechnology, vol. 24, No. 11, 2006, pp. 523-529.
Ferrer, L, et al., "Canine Atopic Dermatitis: Evidence Based Dermatology", The North American Veterinary Conference (NAVC)-2005 Proceedings, Jan. 8-12, 2005, Orlando, Florida, pp. 244-246, [online], [retrieved on May 17, 2016]. Retrieved from the Internet: <URL: http://www.ivis.org/proceedings/navc/2005/SAE/092.pdf?LA=1>.
Fujimori, "A Modeling Analysis of Monoclonal Antibody Percolation Through Tumors: A Binding-Site Barrier", Journal Nuclear Medicine, vol. 31, No. 7, Jul. 1990, pp. 1191-1198.

(56) References Cited

OTHER PUBLICATIONS

Impellizeri, "The Role of Rituximab in the Treatment of Canine Lymphoma: An Ex Vivo Evaluation", The Veterinary Journal, vol. 171, 2006, pp. 556-558.

Kettleborough, et al. "MMHumanization of a mouse monoclonal antibody by CDR-grafting: the importance of framework residues on loop conformation" Protein Eng., vol. 4, No. 7, Nov. 1991, pp. 773-783.

Kumar, S., et al., "Molecular Cloning and Expression of the Fabs of Human Autoantibodies on *Escherichia coli*: Determination of the Heavy or Light Chain Contribution to the Anti-DNA/-Cardiolipin Activity of the Fab", The Journal of Biological Chemistry, vol. 275, No. 45, Nov. 10, 2000, pp. 35129-35136.

Mazza, G., et al., "The Separation and Identification by Monoclonal Antibodies of Dog IgG Fractions", J. Imm Meth., vol. 161, May 1993, pp. 193-203.

Paul, W.E., (Editor) "Structure and Function of Immunoglobulins." in Fundamental Immunology (New York, Raven Press, 1993), 3rd Edition, Ch. 9, pp. 292-295.

Rudnick, "Affinity and Avidity in Antibody-Based Tumor Targeting", Cancer Biotherapy and Radiopharmaceuticals, vol. 24, No. 2, 2009, pp. 155-162 <DOI: 10.1089/cbr.2009.0627>.

Talmadge, "Murine Models to Evaluate Novel and Conventional Therapeutic Strategies for Cancer", The American Journal of Pathology, vol. 170, No. 3, 2007, pp. 793-804.

Thurber, "Antibody Tumor Penetration: Transport Opposed by Systemic and Antigen-Mediated Clearance", Advanced Drug Delivery Reviews, vol. 60, 2008, pp. 1421-1434.

UniProtKB Direct Submission Q28896. CD52_CANFA; Feb. 1, 1998, [online], [retrieved on Mar. 14, 2014]. Retrieved from the Internet: <URL: http://www.ncbi.nlm.nih.gov/protein/3182945?sat=OLDID&satkey=5321424>.

Voskoglou-Nomikos, "Clinical Predictive Value of the In Vitro Cell Line, Human Xenograft, and Mouse Allograft Preclinical Cancer Models", vol. 9, Sep. 2003, pp. 4227-4239.

Winston, et al. "Immunohistochemical detection of HER-2/neu expression in spontaneous feline mammary tumours", Veterinary and Comparative Oncology, vol. 3, No. 1, 2005, pp. 8-15.

* cited by examiner

SEQUENCE LISTING

<160> NUMBER OF SEQ ID NOS: 46

<210> SEQ ID NO 1
<211> LENGTH: 297
<212> TYPE: PRT
<213> ORGANISM: Canis familiaris

<400> SEQUENCE: 1

```
Met Thr Thr Pro Arg Asn Ser Met Ser Gly Thr Leu Pro Val Asp Pro
1               5                   10                  15

Met Lys Ser Pro Thr Ala Met Tyr Pro Val Gln Lys Ile Ile Pro Lys
            20                  25                  30

Arg Met Pro Ser Val Val Gly Pro Thr Gln Asn Phe Phe Met Arg Glu
        35                  40                  45

Ser Lys Thr Leu Gly Ala Val Gln Ile Met Asn Gly Leu Phe His Ile
    50                  55                  60

Ala Leu Gly Ser Leu Leu Met Ile His Thr Asp Val Tyr Ala Pro Ile
65                  70                  75                  80

Cys Ile Thr Met Trp Tyr Pro Leu Trp Gly Gly Ile Met Phe Ile Ile
                85                  90                  95

Ser Gly Ser Leu Leu Ala Ala Asp Lys Asn Pro Arg Lys Ser Leu
                100                 105                 110         Leu

Val Lys Gly Lys Met Ile Met Asn Ser Leu Ser Leu Phe Ala Ala Ile
        115                 120                 125

Ser Gly Ile Ile Phe Leu Ile Met Asp Ile Phe Asn Ile Thr Ile Ser
    130                 135                 140

His Phe Phe Lys Met Glu Asn Leu Asn Leu Ile Lys Ala Pro Met Pro
145                 150                 155                 160

Tyr Val Asp Ile His Asn Cys Asp Pro Ala Asn Pro Ser Glu Lys Asn
                165                 170                 175

Ser Leu Ser Ile Gln Tyr Cys Gly Ser Ile Arg Ser Val Phe Leu Gly
                180                 185                 190

Val Phe Ala Val Met Val Ile Phe Thr Phe Phe Gln Lys Leu Val Thr
            195                 200                 205

Ala Gly Ile Val Glu Asn Glu Trp Lys Lys Leu Cys Ser Lys Pro Lys
        210                 215                 220

Ser Asp Val Val Leu Leu Ala Ala Glu Glu Lys Lys Glu Gln Pro
225                 230                 235                 240

Ile Glu Thr Thr Glu Glu Met Val Glu Leu Thr Glu Ile Ala Ser Gln
                245                 250                 255

Pro Lys Lys Glu Glu Asp Ile Glu Ile Ile Pro Val Gln Glu Glu Glu
            260                 265                 270

Glu Glu Leu Glu Ile Asn Phe Ala Glu Pro Pro Gln Glu Gln Glu Ser
        275                 280                 285

Ser Pro Ile Glu Asn Asp Ser Ile Pro
    290                 295

<210> SEQ ID NO 2
<211> LENGTH: 298
<212> TYPE: PRT
<213> ORGANISM: Felis catus

<400> SEQUENCE: 2

Met Thr Thr Pro Arg Asn Ser Met Ser Gly Thr Leu Pro Ala Asp Ala
1               5                   10                  15

Met Lys Ser Pro Thr Ala Met Asn Pro Val Gln Lys Ile Ile Pro Lys
            20                  25                  30

Lys Met Pro Ser Val Val Gly Pro Thr Gln Asn Phe Phe Met Lys Glu
        35                  40                  45

Ser Lys Pro Leu Gly Ala Val Gln Ile Met Asn Gly Leu Phe His Met
    50                  55                  60

Ala Leu Gly Gly Leu Leu Met Ile His Met Glu Val Tyr Ala Pro Ile
```

```
             65                  70                  75                  80
Cys Met Thr Val Trp Tyr Pro Leu Trp Gly Gly Ile Met Tyr Ile Ile
                     85                  90                  95
Ser Gly Ser Leu Leu Val Ala Ala Glu Lys Asn Pro Arg Lys Ser Leu
                 100                 105                 110
Val Lys Gly Lys Met Ile Met Asn Ser Leu Ser Leu Phe Ala Ala Ile
             115                 120                 125
Ser Gly Met Ile Leu Leu Ile Met Asp Ile Phe Asn Ile Ala Ile Ser
         130                 135                 140
His Phe Phe Lys Met Glu Asn Leu Asn Leu Leu Lys Ser Pro Lys Pro
145                 150                 155                 160
Tyr Ile Asp Ile His Thr Cys Gln Pro Glu Ser Lys Pro Ser Glu Lys
                 165                 170                 175
Asn Ser Leu Ser Ile Lys Tyr Cys Asp Ser Ile Arg Ser Val Phe Leu
             180                 185                 190
Ser Ile Phe Ala Val Met Val Val Phe Thr Leu Phe Gln Lys Leu Val
         195                 200                 205
Thr Ala Gly Ile Val Glu Asn Glu Trp Lys Lys Leu Cys Ser Lys Pro
     210                 215                 220
Lys Ala Asp Val Val Val Leu Leu Ala Ala Glu Lys Lys Glu Gln
225                 230                 235                 240
Leu Val Glu Ile Thr Glu Glu Ala Val Glu Leu Thr Glu Val Ser Ser
                 245                 250                 255
Gln Pro Lys Asn Glu Glu Asp Ile Glu Ile Ile Pro Val Gln Glu Glu
             260                 265                 270
Glu Glu Glu Thr Glu Met Asn Phe Pro Glu Pro Gln Asp Gln Glu
         275                 280                 285
Pro Ser Leu Ile Glu Asn Asp Ser Ile Pro
         290                 295

<210> SEQ ID NO 3
<211> LENGTH: 21
<212> TYPE: DNA
<213> ORGANISM: Felis catus

<400> SEQUENCE: 3
tgagatgaca acacccagaa a                                              21

<210> SEQ ID NO 4
<211> LENGTH: 21
<212> TYPE: DNA
<213> ORGANISM: Canis familiaris

<400> SEQUENCE: 4
ttaagggatg ctgtcgtttt c                                              21

<210> SEQ ID NO 5
<211> LENGTH: 25
<212> TYPE: DNA
<213> ORGANISM: Canis familiaris

<400> SEQUENCE: 5
aatattacca tttcccattt tttta                                          25

<210> SEQ ID NO 6
<211> LENGTH: 23
<212> TYPE: DNA
<213> ORGANISM: Canis familiaris
```

```
<400> SEQUENCE: 6
tatgctgcca caatattgta tag                                            23

<210> SEQ ID NO 7
<211> LENGTH: 26
<212> TYPE: DNA
<213> ORGANISM: Felis catus

<400> SEQUENCE: 7
ggatccttaa ggaatgctat cgtttt                                         26

<210> SEQ ID NO 8
<211> LENGTH: 333
<212> TYPE: PRT
<213> ORGANISM: Canis familiaris

<400> SEQUENCE: 8
```

Ala Ser Thr Thr Ala Pro Ser Val Phe Pro Leu Ala Pro Ser Cys Gly
1               5                   10                  15

Ser Gln Ser Gly Ser Thr Val Ala Leu Ala Cys Leu Val Ser Gly Tyr
            20                  25                  30

Ile Pro Glu Pro Val Thr Val Ser Trp Asn Ser Gly Ser Leu Thr Ser
        35                  40                  45

Gly Val His Thr Phe Pro Ser Ile Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Thr Asn Thr Lys Val Asp Lys
                85                  90                  95

Pro Val Val Lys Glu Cys Glu Cys Lys Cys Asn Cys Asn Asn Cys Pro
            100                 105                 110

Cys Pro Gly Cys Gly Leu Leu Gly Gly Pro Ser Val Phe Ile Phe Pro
        115                 120                 125

Pro Lys Pro Lys Asp Ile Leu Val Thr Ala Arg Thr Pro Thr Val Thr
    130                 135                 140

Cys Val Val Val Asp Leu Asp Pro Glu Asn Pro Glu Val Gln Ile Ser
145                 150                 155                 160

Trp Phe Val Asp Ser Lys Gln Val Gln Thr Ala Asn Thr Gln Pro Arg
                165                 170                 175

Glu Glu Gln Ser Asn Gly Thr Tyr Arg Val Val Ser Val Leu Pro Ile
            180                 185                 190

Gly His Gln Asp Trp Leu Ser Gly Lys Gln Phe Lys Cys Lys Val Asn
        195                 200                 205

Asn Lys Ala Leu Pro Ser Pro Ile Glu Glu Ile Ile Ser Lys Thr Pro
    210                 215                 220

Gly Gln Ala His Gln Pro Asn Val Tyr Val Leu Pro Pro Ser Arg Asp
225                 230                 235                 240

Glu Met Ser Lys Asn Thr Val Thr Leu Thr Cys Leu Val Lys Asp Phe
                245                 250                 255

Phe Pro Pro Glu Ile Asp Val Glu Trp Gln Ser Asn Gly Gln Gln Glu
            260                 265                 270

Pro Glu Ser Lys Tyr Arg Met Thr Pro Pro Gln Leu Asp Glu Asp Gly
        275                 280                 285

Ser Tyr Phe Leu Tyr Ser Lys Leu Ser Val Asp Lys Ser Arg Trp Gln
    290                 295                 300

Arg Gly Asp Thr Phe Ile Cys Ala Val Met His Glu Ala Leu His Asn
305                 310                 315                 320

His Tyr Thr Gln Lys Ser Leu Ser His Ser Pro Gly Lys
            325                 330

<210> SEQ ID NO 9
<211> LENGTH: 335
<212> TYPE: PRT
<213> ORGANISM: Canis familiaris

<400> SEQUENCE: 9

Ala Ser Thr Thr Ala Pro Ser Val Phe Pro Leu Ala Pro Ser Cys Gly
1               5                   10                  15

Ser Gln Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335

<210> SEQ ID NO 10
<211> LENGTH: 335
<212> TYPE: PRT
<213> ORGANISM: Canis familiaris

<400> SEQUENCE: 10

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335

<210> SEQ ID NO 11
<211> LENGTH: 335
<212> TYPE: PRT
<213> ORGANISM: Canis familiaris

<400> SEQUENCE: 11

Ala Ser Thr Thr Ala Pro Ser Val Phe Pro Leu Ala Pro Ser Cys Gly

```
            1               5                  10                  15
    Ser Thr Ser Gly Ser Thr Val Ala Leu Ala Cys Leu Val Ser Gly Tyr
                    20                  25                  30

Phe Pro Glu Pro Val Thr Val Ser Trp Asn Ser Gly Ser Leu Thr Ser
                    35                  40                  45

Gly Val His Thr Phe Pro Ser Val Leu Gln Ser Ser Gly Leu Tyr Ser
                    50                  55                  60

Leu Ser Ser Met Val Thr Val Pro Ser Ser Arg Trp Pro Ser Glu Thr
    65                  70                  75                  80

Phe Thr Cys Asn Val Ala His Pro Ala Ser Lys Thr Lys Val Asp Lys
                    85                  90                  95

Pro Val Pro Lys Arg Glu Asn Gly Arg Val Pro Arg Pro Pro Asp Cys
                    100                 105                 110

Pro Lys Cys Pro Ala Pro Glu Met Leu Gly Gly Pro Ser Val Phe Ile
                    115                 120                 125

Phe Pro Pro Lys Pro Lys Asp Thr Leu Leu Ile Ala Arg Thr Pro Glu
                    130                 135                 140

Val Thr Cys Val Val Asp Leu Asp Pro Glu Asp Pro Glu Val Gln
    145                 150                 155                 160

Ile Ser Trp Phe Val Asp Gly Lys Gln Met Gln Thr Ala Lys Thr Gln
                    165                 170                 175

Pro Arg Glu Glu Gln Phe Asn Gly Thr Tyr Arg Val Val Ser Val Leu
                    180                 185                 190

Pro Ile Gly His Gln Asp Trp Leu Lys Gly Lys Gln Phe Thr Cys Lys
                    195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
    225                 230                 235                 240

Arg Glu Glu Leu Ser Lys Asn Thr Val Ser Leu Thr Cys Leu Ile Lys
                    245                 250                 255

Asp Phe Phe Pro Pro Asp Ile Asp Val Glu Trp Gln Ser Asn Gly Gln
                    260                 265                 270

Gln Glu Pro Glu Ser Lys Tyr Arg Thr Thr Pro Pro Gln Leu Asp Glu
                    275                 280                 285

Asp Gly Ser Tyr Phe Leu Tyr Ser Lys Leu Ser Val Asp Lys Ser Arg
                    290                 295                 300

Trp Gln Arg Gly Asp Thr Phe Ile Cys Ala Val Met His Glu Ala Leu
    305                 310                 315                 320

His Asn His Tyr Thr Gln Lys Ser Leu Ser His Ser Pro Gly Lys
                    325                 330                 335
```

<210> SEQ ID NO 12
<211> LENGTH: 335
<212> TYPE: PRT
<213> ORGANISM: Canis familiaris

<400> SEQUENCE: 12

```
            1               5                  10                  15
    Ala Ser Thr Thr Ala Pro Ser Val Phe Pro Leu Ala Pro Ser Cys Gly
                                        10                  15

Ser Thr Ser Gly Ser Thr Val Ala Leu Ala Cys Leu Val Ser Gly Tyr
                    20                  25                  30

Phe Pro Glu Pro Val Thr Val Ser Trp Asn Ser Gly Ser Leu Thr Ser
                    35                  40                  45
```

```
Gly Val His Thr Phe Pro Ser Val Leu Gln Ser Ser Gly Leu Tyr Ser
 50                  55                  60

Leu Ser Ser Met Val Thr Val Pro Ser Ser Arg Trp Pro Ser Glu Thr
 65                  70                  75                  80

Phe Thr Cys Asn Val Ala His Pro Ala Ser Lys Thr Lys Val Asp Lys
                 85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
            115                 120                 125

Phe Pro Pro Lys Pro Lys Asp Thr Leu Leu Ile Ala Arg Thr Pro Glu
130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
            195                 200                 205

Val Asn Asn Lys Ala Leu Pro Ser Pro Ile Glu Arg Thr Ile Ser Lys
210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
            275                 280                 285

Asp Gly Ser Tyr Phe Leu Tyr Ser Lys Leu Ser Val Asp Lys Ser Arg
290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335

<210> SEQ ID NO 13
<211> LENGTH: 333
<212> TYPE: PRT
<213> ORGANISM: Canis familiaris

<400> SEQUENCE: 13

Ala Ser Thr Thr Ala Pro Ser Val Phe Pro Leu Ala Pro Ser Cys Gly
 1               5                  10                  15

Ser Gln Ser Gly Ser Thr Val Ala Leu Ala Cys Leu Val Ser Gly Tyr
             20                  25                  30

Ile Pro Glu Pro Val Thr Val Ser Trp Asn Ser Gly Ser Leu Thr Ser
         35                  40                  45

Gly Val His Thr Phe Pro Ser Ile Leu Gln Ser Ser Gly Leu Tyr Ser
 50                  55                  60

Leu Ser Ser Met Val Thr Val Pro Ser Ser Arg Trp Pro Ser Glu Thr
 65                  70                  75                  80

Phe Thr Cys Asn Val Ala His Pro Ala Thr Asn Thr Lys Val Asp Lys
                 85                  90                  95
```

Pro Val Val Lys Glu Cys Glu Cys Lys Cys Asn Cys Asn Asn Cys Pro
            100                 105                 110

Cys Pro Gly Cys Gly Leu Leu Gly Pro Ser Val Phe Ile Phe Pro
        115                 120                 125

Pro Lys Pro Lys Asp Ile Leu Val Thr Ala Arg Thr Pro Thr Val Thr
    130                 135                 140

Cys Val Val Asp Leu Asp Pro Glu Asn Pro Glu Val Gln Ile Ser
145                 150                 155                 160

Trp Phe Val Asp Gly Lys Gln Met Gln Thr Ala Lys Thr Gln Pro Arg
                165                 170                 175

Glu Glu Gln Phe Asn Gly Thr Tyr Arg Val Val Ser Val Leu Pro Ile
            180                 185                 190

Gly His Gln Asp Trp Leu Lys Gly Lys Gln Phe Thr Cys Lys Val Asn
        195                 200                 205

Asn Lys Ala Leu Pro Ser Pro Ile Glu Arg Thr Ile Ser Lys Ala Arg
    210                 215                 220

Gly Gln Ala His Gln Pro Ser Val Tyr Val Leu Pro Pro Ser Arg Glu
225                 230                 235                 240

Glu Leu Ser Lys Asn Thr Val Ser Leu Thr Cys Leu Ile Lys Asp Phe
                245                 250                 255

Phe Pro Pro Asp Ile Asp Val Glu Trp Gln Ser Asn Gly Gln Gln Glu
            260                 265                 270

Pro Glu Ser Lys Tyr Arg Thr Thr Pro Pro Gln Leu Asp Glu Asp Gly
        275                 280                 285

Ser Tyr Phe Leu Tyr Ser Lys Leu Ser Val Asp Lys Ser Arg Trp Gln
    290                 295                 300

Arg Gly Asp Thr Phe Ile Cys Ala Val Met His Glu Ser Leu His Asn
305                 310                 315                 320

His Tyr Thr Gln Lys Ser Leu Ser His Ser Pro Gly Lys
                325                 330

<210> SEQ ID NO 14
<211> LENGTH: 335
<212> TYPE: PRT
<213> ORGANISM: Canis familiaris

<400> SEQUENCE: 14

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Tyr Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Gly Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu

```
                130                 135                 140
Val Thr Cys Val Val Asp Leu Asp Pro Glu Asp Pro Glu Val Gln
145                 150                 155                 160

Ile Ser Trp Phe Val Asp Ser Lys Gln Val Gln Thr Ala Asn Thr Gln
                165                 170                 175

Pro Arg Glu Glu Gln Ser Asn Gly Thr Tyr Arg Val Val Ser Val Leu
            180                 185                 190

Pro Ile Gly His Gln Asp Trp Leu Ser Gly Lys Gln Phe Lys Cys Lys
            195                 200                 205

Val Asn Asn Lys Ala Leu Pro Ser Pro Ile Glu Glu Ile Ser Lys
            210                 215                 220

Thr Pro Gly Gln Ala His Gln Pro Asn Val Tyr Val Leu Pro Pro Ser
225                 230                 235                 240

Arg Asp Glu Met Ser Lys Asn Thr Val Thr Leu Thr Cys Leu Val Lys
                245                 250                 255

Asp Phe Phe Pro Pro Glu Ile Asp Val Glu Trp Gln Ser Asn Gly Gln
            260                 265                 270

Gln Glu Pro Glu Ser Lys Tyr Arg Met Thr Pro Pro Gln Leu Asp Glu
            275                 280                 285

Asp Gly Ser Tyr Phe Leu Tyr Ser Lys Leu Ser Val Asp Lys Ser Arg
            290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335

<210> SEQ ID NO 15
<211> LENGTH: 109
<212> TYPE: PRT
<213> ORGANISM: Canis familiaris

<400> SEQUENCE: 15

Asn Asp Ala Gln Pro Ala Val Tyr Leu Phe Gln Pro Ser Pro Asp Gln
1               5                   10                  15

Leu His Thr Gly Ser Ala Ser Val Val Cys Leu Leu Asn Ser Phe Tyr
                20                  25                  30

Pro Lys Asp Ile Asn Val Lys Trp Lys Val Asp Gly Val Ile Gln Asp
            35                  40                  45

Thr Gly Ile Gln Glu Ser Val Thr Glu Gln Asp Lys Asp Ser Thr Tyr
        50                  55                  60

Ser Leu Ser Ser Thr Leu Thr Met Ser Ser Thr Glu Tyr Leu Ser His
65                  70                  75                  80

Glu Leu Tyr Ser Cys Glu Ile Thr His Lys Ser Leu Pro Ser Thr Leu
                85                  90                  95

Ile Lys Ser Phe Gln Arg Ser Glu Cys Gln Arg Val Asp
            100                 105

<210> SEQ ID NO 16
<211> LENGTH: 106
<212> TYPE: PRT
<213> ORGANISM: Canis familiaris

<400> SEQUENCE: 16

Gly Gln Pro Lys Ala Ser Pro Ser Val Thr Leu Phe Pro Pro Ser Ser
1               5                   10                  15

Glu Glu Leu Gly Ala Asn Lys Ala Thr Leu Val Cys Leu Ile Ser Asp
```

```
                    20                  25                  30
Phe Tyr Pro Ser Gly Val Thr Val Ala Trp Lys Ala Asp Gly Ser Pro
                35                  40                  45

Ile Thr Gln Gly Val Glu Thr Thr Lys Pro Ser Lys Gln Ser Asn Asn
             50                  55                  60

Lys Tyr Ala Ala Ser Ser Tyr Leu Ser Leu Thr Pro Asp Lys Trp Lys
 65                  70                  75                  80

Ser His Ser Ser Phe Ser Cys Leu Val Thr His Glu Gly Ser Thr Val
                 85                  90                  95

Glu Lys Lys Val Ala Pro Ala Glu Cys Ser
            100                 105

<210> SEQ ID NO 17
<211> LENGTH: 111
<212> TYPE: PRT
<213> ORGANISM: Artificial Sequence
<220> FEATURE:
<223> OTHER INFORMATION: canis familiaris/mus musculus

<400> SEQUENCE: 17

Glu Ile Gln Leu Gln Gln Ser Gly Ala Glu Leu Val Lys Pro Gly Ala
  1               5                  10                  15

Ser Val Lys Ile Ser Cys Lys Ala Ser Gly Tyr Thr Phe Thr Asp Tyr
                 20                  25                  30

Tyr Ile Asn Trp Val Lys Gln Arg Pro Gly Gln Gly Leu Glu Trp Ile
                 35                  40                  45

Gly Lys Ile Gly Pro Gly Ser Gly Arg Thr Tyr Tyr Asn Glu Lys Phe
 50                  55                  60

Lys Gly Lys Ala Thr Leu Thr Ala Asp Lys Ser Ser Ser Thr Ala Tyr
 65                  70                  75                  80

Ile Gln Ile Ser Ser Leu Thr Ser Glu Asp Ser Ala Val Tyr Phe Cys
                 85                  90                  95

Ala Val Leu Ser Trp Gly Gln Gly Thr Thr Leu Thr Val Ser Ser
            100                 105                 110

<210> SEQ ID NO 18
<211> LENGTH: 111
<212> TYPE: PRT
<213> ORGANISM: Artificial Sequence
<220> FEATURE:
<223> OTHER INFORMATION: canis familiaris/mus musculus

<400> SEQUENCE: 18

Glu Ile Gln Leu Gln Gln Ser Gly Ala Glu Leu Val Lys Pro Gly Ala
  1               5                  10                  15

Ser Val Lys Ile Ser Cys Lys Ala Ser Gly Tyr Thr Phe Thr Asp Tyr
                 20                  25                  30

Tyr Ile Asn Trp Val Lys Gln Arg Pro Gly Gln Gly Leu Glu Trp Ile
                 35                  40                  45

Gly Lys Ile Gly Pro Gly Ser Gly Arg Thr Tyr Tyr Asn Glu Lys Phe
 50                  55                  60

Lys Gly Lys Ala Thr Leu Thr Ala Asp Lys Ser Ser Ser Thr Ala Tyr
 65                  70                  75                  80

Ile Gln Ile Ser Ser Leu Thr Ser Glu Asp Ser Ala Val Tyr Phe Cys
                 85                  90                  95

Ala Val Leu Ser Trp Gly Gln Gly Thr Leu Val Thr Val Ser Ser
            100                 105                 110
```

```
<210> SEQ ID NO 19
<211> LENGTH: 111
<212> TYPE: PRT
<213> ORGANISM: Artificial Sequence
<220> FEATURE:
<223> OTHER INFORMATION: canis familiaris/mus musculus

<400> SEQUENCE: 19

Glu Val Gln Leu Val Glu Ser Gly Gly Asp Leu Val Lys Pro Gly Gly
1               5                   10                  15

Ser Leu Arg Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Lys Ile Gly Pro Gly Ser Gly Arg Thr Tyr Tyr Asn Glu Lys Phe
    50                  55                  60

Lys Gly Lys Ala Thr Leu Thr Ala Asp Lys Ser Ser Thr Ala Tyr
65                  70                  75                  80

Ile Gln Ile Ser Ser Leu Thr Ser Glu Asp Ser Ala Val Tyr Phe Cys
                85                  90                  95

Ala Val Leu Ser Trp Gly Gln Gly Thr Leu Val Thr Val Ser Ser
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: canis familiaris/mus musculus

<400> SEQUENCE: 20

Asp Val Gln Ile Thr Gln Thr Pro Leu Thr Leu Ser Val Thr Phe Gly
1               5                   10                  15

Gln Pro Ala Ser Ile Ser Cys Lys Ser Ser Gln Ser Leu Leu Lys Ser
            20                  25                  30

Asp Gly Arg Thr Tyr Leu Asn Trp Leu Leu Gln Arg Pro Gly Gln Ser
        35                  40                  45

Pro Lys Arg Leu Leu Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: canis familiaris/mus musculus

<400> SEQUENCE: 21

Asp Val Gln Ile Thr Gln Thr Pro Leu Thr Leu Ser Val Thr Phe Gly
1               5                   10                  15

Gln Pro Ala Ser Ile Ser Cys Lys Ser Ser Gln Ser Leu Leu Lys Ser
            20                  25                  30

Asp Gly Arg Thr Tyr Leu Asn Trp Leu Leu Gln Arg Pro Gly Gln Ser
```

```
            35                  40                  45

Pro Lys Arg Leu Leu Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr His Leu Thr Val Leu
                100                 105                 110

<210> SEQ ID NO 22
<211> LENGTH: 111
<212> TYPE: PRT
<213> ORGANISM: Artificial Sequence
<220> FEATURE:
<223> OTHER INFORMATION: canis familiaris/mus musculus

<400> SEQUENCE: 22

Gln Ser Val Leu Thr Gln Pro Ala Ser Val Ser Gly Ser Leu Gly Gln
1               5                   10                  15

Arg Val Thr Ile Ser Cys Lys Ser Ser Gln Ser Leu Leu Lys Ser Asp
                20                  25                  30

Gly Arg Thr Tyr Leu Asn Trp Leu Leu Gln Arg Pro Gly Gln Ser Pro
            35                  40                  45

Lys Arg Leu Leu Tyr Leu Val Ser Lys Leu Asp Ser Gly Val Pro Asp
    50                  55                  60

Arg Phe Thr Gly Ser Gly Ser Gly Thr Asp Phe Thr Leu Lys Ile Ser
65                  70                  75                  80

Arg Val Glu Ala Glu Asp Leu Gly Val Tyr Tyr Cys Trp Gln Gly Thr
                85                  90                  95

His Phe Pro Gln Thr Phe Gly Gly Gly Thr His Leu Thr Val Leu
                100                 105                 110

<210> SEQ ID NO 23
<211> LENGTH: 113
<212> TYPE: PRT
<213> ORGANISM: Artificial Sequence
<220> FEATURE:
<223> OTHER INFORMATION: canis familiaris/mus musculus

<400> SEQUENCE: 23

Gln Val Gln Leu Gln Gln Ser Arg Ala Glu Leu Val Arg Pro Gly Ala
1               5                   10                  15

Ser Val Thr Leu Ser Cys Lys Pro Ser Gly Tyr Thr Phe Thr Asp Tyr
                20                  25                  30

Glu Val His Trp Val Lys Gln Thr Pro Val His Gly Leu Glu Trp Ile
            35                  40                  45

Gly Ala Ile Asp Pro Glu Thr Gly Gly Thr Ala Asp Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Asn Phe Val Asp Val Trp Gly Thr Gly Thr Thr Val Thr Val Ser
                100                 105                 110

Ser
```

<210> SEQ ID NO 24
<211> LENGTH: 113
<212> TYPE: PRT
<213> ORGANISM: Artificial Sequence
<220> FEATURE:
<223> OTHER INFORMATION: canis familiaris/mus musculus

<400> SEQUENCE: 24

```
Asp Val Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Phe Tyr Cys Gln Gln
                85                  90                  95

Tyr Tyr Asn Tyr Pro Leu Thr Phe Gly Ala Gly Thr Lys Leu Glu Leu
                100                 105                 110

Lys
```

<210> SEQ ID NO 25
<211> LENGTH: 113
<212> TYPE: PRT
<213> ORGANISM: Artificial Sequence
<220> FEATURE:
<223> OTHER INFORMATION: canis familiaris/mus musculus

<400> SEQUENCE: 25

```
Asp Val Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Phe Tyr Cys Gln Gln
                85                  90                  95

Tyr Tyr Asn Tyr Pro Leu Thr Phe Gly Gly Gly Thr His Leu Thr Val
                100                 105                 110

Leu
```

<210> SEQ ID NO 26
<211> LENGTH: 113
<212> TYPE: PRT
<213> ORGANISM: Artificial Sequence
<220> FEATURE:
<223> OTHER INFORMATION: canis familiaris/mus musculus

<400> SEQUENCE: 26

```
Asp Ile Val Thr Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
```

```
                20                  25                  30
Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Leu Thr Phe Gly Gly Gly Thr His Leu Thr Val
            100                 105                 110

Leu

<210> SEQ ID NO 27
<211> LENGTH: 114
<212> TYPE: PRT
<213> ORGANISM: Artificial Sequence
<220> FEATURE:
<223> OTHER INFORMATION: canis familiaris/mus musculus

<400> SEQUENCE: 27

Glu Val Gln Leu Gln Gln Ser Val Ala Glu Leu Val Arg Pro Gly Ala
1               5                   10                  15

Ser Val Thr Leu Ser Cys Lys Ala Ser Gly Tyr Thr Phe Thr Asp Tyr
                20                  25                  30

Glu Met His Trp Val Lys Gln Thr Pro Val His Gly Leu Glu Trp Ile
            35                  40                  45

Gly Glu Ile Asp Pro Glu Thr Gly Gly Thr Ala Tyr Asn Gln Lys Phe
        50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Glu Tyr Ala Met Asp Tyr Trp Gly Gln Gly Thr Leu Val Thr Val
            100                 105                 110

Ser Ser

<210> SEQ ID NO 28
<211> LENGTH: 113
<212> TYPE: PRT
<213> ORGANISM: Artificial Sequence
<220> FEATURE:
<223> OTHER INFORMATION: canis familiaris/mus musculus

<400> SEQUENCE: 28

Asp Ile Val Thr Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95
```

Tyr Tyr Asn Tyr Pro Leu Thr Phe Gly Ala Gly Thr Lys Leu Glu Leu
            100                 105                 110

Lys

<210> SEQ ID NO 29
<211> LENGTH: 114
<212> TYPE: PRT
<213> ORGANISM: Artificial Sequence
<220> FEATURE:
<223> OTHER INFORMATION: canis familiaris/mus musculus

<400> SEQUENCE: 29

Glu Val Gln Leu Gln Gln Ser Val Ala Glu Leu Val Arg Pro Gly Ala
1               5                   10                  15

Ser Val Thr Leu Ser Cys Lys Ala Ser Gly Tyr Thr Phe Thr Asp Tyr
                20                  25                  30

Glu Met His Trp Val Lys Gln Thr Pro Val His Gly Leu Glu Trp Ile
            35                  40                  45

Gly Glu Ile Asp Pro Glu Thr Gly Gly Thr Ala Tyr Asn Gln Lys Phe
        50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Glu Tyr Ala Met Asp Tyr Trp Gly Gln Gly Thr Ser Val Thr Val
            100                 105                 110

Ser Ser

<210> SEQ ID NO 30
<211> LENGTH: 111
<212> TYPE: PRT
<213> ORGANISM: Artificial Sequence
<220> FEATURE:
<223> OTHER INFORMATION: canis familiaris/mus musculus

<400> SEQUENCE: 30

Arg Val Gln Leu Lys Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Asn Trp Val Lys Gln Arg Pro Gly Gln Gly Leu Glu Trp Ile
            35                  40                  45

Gly Lys Ile Gly Pro Arg Ser Gly Ser Ile Tyr Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Gln Leu Arg Ser Leu Thr Ser Glu Asp Ser Ala Val Tyr Phe Cys
                85                  90                  95

Ala Val Leu Lys Trp Gly Gln Gly Thr Leu Val Thr Val Ser Ser
            100                 105                 110

<210> SEQ ID NO 31
<211> LENGTH: 111
<212> TYPE: PRT
<213> ORGANISM: Artificial Sequence
<220> FEATURE:
<223> OTHER INFORMATION: canis familiaris/mus musculus

<400> SEQUENCE: 31

```
Gln Val Gln Leu Lys Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Lys Ile Gly Pro Arg Ser Gly Ser Ile Tyr Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Arg Ser Leu Thr Ser Glu Asp Ser Ala Val Tyr Phe Cys
                85                  90                  95

Ala Val Leu Lys Trp Gly Gln Gly Thr Leu Val Thr Val Ser Ser
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: canis familiaris/mus musculus

<400> SEQUENCE: 32

Asp Ala Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: canis familiaris/mus musculus

<400> SEQUENCE: 33

Asp Ala Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
```

```
                    85                  90                  95

Thr His Phe Pro Gln Thr Phe Gly Gly Gly Thr His Leu Thr Val Leu
            100                 105                 110

<210> SEQ ID NO 34
<211> LENGTH: 116
<212> TYPE: PRT
<213> ORGANISM: Artificial Sequence
<220> FEATURE:
<223> OTHER INFORMATION: canis familiaris/mus musculus

<400> SEQUENCE: 34

Glu Ile Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Val Tyr
65                  70                  75                  80

Met Glu Leu Arg Ser Leu Thr Ser Glu Asp Ser Ala Val Tyr Tyr Cys
                85                  90                  95

Thr Arg Asp Tyr Gly Thr Ser Gly Tyr Trp Gly Gln Gly Thr Thr Leu
            100                 105                 110

Thr Val Ser Ser
        115

<210> SEQ ID NO 35
<211> LENGTH: 116
<212> TYPE: PRT
<213> ORGANISM: Artificial Sequence
<220> FEATURE:
<223> OTHER INFORMATION: canis familiaris/mus musculus

<400> SEQUENCE: 35

Glu Ile Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Val Tyr
65                  70                  75                  80

Met Glu Leu Arg Ser Leu Thr Ser Glu Asp Ser Ala Val Tyr Tyr Cys
                85                  90                  95

Thr Arg Asp Tyr Gly Thr Ser Gly Tyr Trp Gly Gln Gly Thr Leu Val
            100                 105                 110

Thr Val Ser Ser
        115

<210> SEQ ID NO 36
<211> LENGTH: 112
<212> TYPE: PRT
<213> ORGANISM: Artificial Sequence
<220> FEATURE:
```

<223> OTHER INFORMATION: canis familiaris/mus musculus

<400> SEQUENCE: 36

Asp Val Val Val Thr Gln Thr Pro Leu Ser Leu Pro Val Ser Phe Gly
1               5                   10                  15

Asp Gln Val Ser Ile Ser Cys Arg Ser Ser Gln Ser Leu Ala Asn Ser
            20                  25                  30

Tyr Gly Asn Thr Tyr Leu Ser Trp Tyr Leu His Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 37
<211> LENGTH: 112
<212> TYPE: PRT
<213> ORGANISM: Artificial Sequence
<220> FEATURE:
<223> OTHER INFORMATION: canis familiaris/mus musculus

<400> SEQUENCE: 37

Asp Val Val Val Thr Gln Thr Pro Leu Ser Leu Pro Val Ser Phe Gly
1               5                   10                  15

Asp Gln Val Ser Ile Ser Cys Arg Ser Ser Gln Ser Leu Ala Asn Ser
            20                  25                  30

Tyr Gly Asn Thr Tyr Leu Ser Trp Tyr Leu His Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr His Leu Thr Val Leu
            100                 105                 110

<210> SEQ ID NO 38
<211> LENGTH: 448
<212> TYPE: PRT
<213> ORGANISM: Artificial Sequence
<220> FEATURE:
<223> OTHER INFORMATION: canis familiaris/mus musculus

<400> SEQUENCE: 38

Gln Val Gln Leu Gln Gln Ser Arg Ala Glu Leu Val Arg Pro Gly Ala
1               5                   10                  15

Ser Val Thr Leu Ser Cys Lys Pro Ser Gly Tyr Thr Phe Thr Asp Tyr
            20                  25                  30

Glu Val His Trp Val Lys Gln Thr Pro Val His Gly Leu Glu Trp Ile
        35                  40                  45

Gly Ala Ile Asp Pro Glu Thr Gly Gly Thr Ala Asp Asn Gln Lys Phe
    50                  55                  60

Lys Gly Lys Ala Ile Leu Thr Ala Asp Lys Ser Ser Ser Thr Ala Tyr

```
                65                  70                  75                  80
        Met Glu Leu Arg Ser Leu Thr Ser Glu Asp Ser Ala Val Tyr Tyr Cys
                        85                  90                  95

Thr Asn Phe Val Asp Val Trp Gly Thr Gly Thr Thr Val Thr Val Ser
                        100                 105                 110

Ser Ala Ser Thr Thr Ala Pro Ser Val Phe Pro Leu Ala Pro Ser Cys
                        115                 120                 125

Gly Ser Gln Ser Gly Ser Thr Val Ala Leu Ala Cys Leu Val Ser Gly
                        130                 135                 140

Tyr Phe Pro Glu Pro Val Thr Val Ser Trp Asn Ser Gly Ser Leu Thr
        145                 150                 155                 160

Ser Gly Val His Thr Phe Pro Ser Val Leu Gln Ser Ser Gly Leu Tyr
                        165                 170                 175

Ser Leu Ser Ser Met Val Thr Val Pro Ser Ser Arg Trp Pro Ser Glu
                        180                 185                 190

Thr Phe Thr Cys Asn Val Ala His Pro Ala Ser Lys Thr Lys Val Asp
                        195                 200                 205

Lys Pro Val Pro Lys Arg Glu Asn Gly Arg Val Pro Arg Pro Pro Asp
        210                 215                 220

Cys Pro Lys Cys Pro Ala Pro Glu Met Leu Gly Gly Pro Ser Val Phe
        225                 230                 235                 240

Ile Phe Pro Pro Lys Pro Lys Asp Thr Leu Leu Ile Ala Arg Thr Pro
                        245                 250                 255

Glu Val Thr Cys Val Val Val Asp Leu Asp Pro Glu Asp Pro Glu Val
                        260                 265                 270

Gln Ile Ser Trp Phe Val Asp Gly Lys Gln Met Gln Thr Ala Lys Thr
                        275                 280                 285

Gln Pro Arg Glu Glu Gln Phe Asn Gly Thr Tyr Arg Val Val Ser Val
                        290                 295                 300

Leu Pro Ile Gly His Gln Asp Trp Leu Lys Gly Lys Gln Phe Thr Cys
        305                 310                 315                 320

Lys Val Asn Asn Lys Ala Leu Pro Ser Pro Ile Glu Arg Thr Ile Ser
                        325                 330                 335

Lys Ala Arg Gly Gln Ala His Gln Pro Ser Val Tyr Val Leu Pro Pro
                        340                 345                 350

Ser Arg Glu Glu Leu Ser Lys Asn Thr Val Ser Leu Thr Cys Leu Ile
                        355                 360                 365

Lys Asp Phe Phe Pro Pro Asp Ile Asp Val Glu Trp Gln Ser Asn Gly
                        370                 375                 380

Gln Gln Glu Pro Glu Ser Lys Tyr Arg Thr Thr Pro Pro Gln Leu Asp
        385                 390                 395                 400

Glu Asp Gly Ser Tyr Phe Leu Tyr Ser Lys Leu Ser Val Asp Lys Ser
                        405                 410                 415

Arg Trp Gln Arg Gly Asp Thr Phe Ile Cys Ala Val Met His Glu Ala
                        420                 425                 430

Leu His Asn His Tyr Thr Gln Lys Ser Leu Ser His Ser Pro Gly Lys
                        435                 440                 445

<210> SEQ ID NO 39
<211> LENGTH: 219
<212> TYPE: PRT
<213> ORGANISM: Artificial Sequence
<220> FEATURE:
<223> OTHER INFORMATION: canis familiaris/mus musculus
```

```
<400> SEQUENCE: 39

Asp Val Met Ser Gln Ser Pro Ser Leu Ala Val Ser Val Gly
 1               5                  10                  15

Glu Lys Val Thr Met Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Phe Tyr Cys Gln Gln
                85                  90                  95

Tyr Tyr Asn Tyr Pro Leu Thr Phe Gly Gly Gly Thr His Leu Thr Val
            100                 105                 110

Leu Gly Gln Pro Lys Ala Ser Pro Ser Val Thr Leu Phe Pro Pro Ser
        115                 120                 125

Ser Glu Glu Leu Gly Ala Asn Lys Ala Thr Leu Val Cys Leu Ile Ser
    130                 135                 140

Asp Phe Tyr Pro Ser Gly Val Thr Val Ala Trp Lys Ala Asp Gly Ser
145                 150                 155                 160

Pro Ile Thr Gln Gly Val Glu Thr Thr Lys Pro Ser Lys Gln Ser Asn
                165                 170                 175

Asn Lys Tyr Ala Ala Ser Ser Tyr Leu Ser Leu Thr Pro Asp Lys Trp
            180                 185                 190

Lys Ser His Ser Ser Phe Ser Cys Leu Val Thr His Glu Gly Ser Thr
        195                 200                 205

Val Glu Lys Lys Val Ala Pro Ala Glu Cys Ser
    210                 215

<210> SEQ ID NO 40
<211> LENGTH: 446
<212> TYPE: PRT
<213> ORGANISM: Artificial Sequence
<220> FEATURE:
<223> OTHER INFORMATION: canis familiaris/mus musculus

<400> SEQUENCE: 40

Gln Val Gln Leu Lys Gln Ser Gly Ala Glu Leu Val Lys Pro Gly Ala
 1               5                  10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Lys Ile Gly Pro Arg Ser Gly Ser Ile Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Arg Ser Leu Thr Ser Glu Asp Ser Ala Val Tyr Phe Cys
                85                  90                  95

Ala Val Leu Lys Trp Gly Gln Gly Thr Leu Val Thr Val Ser Ser Ala
            100                 105                 110

Ser Thr Thr Ala Pro Ser Val Phe Pro Leu Ala Pro Ser Cys Gly Ser
        115                 120                 125

Gln Ser Gly Ser Thr Val Ala Leu Ala Cys Leu Val Ser Gly Tyr Phe
```

```
            130                 135                 140
Pro Glu Pro Val Thr Val Ser Trp Asn Ser Gly Ser Leu Thr Ser Gly
145                 150                 155                 160

Val His Thr Phe Pro Ser Val Leu Gln Ser Ser Gly Leu Tyr Ser Leu
                165                 170                 175

Ser Ser Met Val Thr Val Pro Ser Ser Arg Trp Pro Ser Glu Thr Phe
            180                 185                 190

Thr Cys Asn Val Ala His Pro Ala Ser Lys Thr Lys Val Asp Lys Pro
        195                 200                 205

Val Pro Lys Arg Glu Asn Gly Arg Val Pro Arg Pro Asp Cys Pro
210                 215                 220

Lys Cys Pro Ala Pro Glu Met Leu Gly Gly Pro Ser Val Phe Ile Phe
225                 230                 235                 240

Pro Pro Lys Pro Lys Asp Thr Leu Leu Ile Ala Arg Thr Pro Glu Val
                245                 250                 255

Thr Cys Val Val Val Asp Leu Asp Pro Glu Asp Pro Glu Val Gln Ile
            260                 265                 270

Ser Trp Phe Val Asp Gly Lys Gln Met Gln Thr Ala Lys Thr Gln Pro
        275                 280                 285

Arg Glu Glu Gln Phe Asn Gly Thr Tyr Arg Val Val Ser Val Leu Pro
290                 295                 300

Ile Gly His Gln Asp Trp Leu Lys Gly Lys Gln Phe Thr Cys Lys Val
305                 310                 315                 320

Asn Asn Lys Ala Leu Pro Ser Pro Ile Glu Arg Thr Ile Ser Lys Ala
                325                 330                 335

Arg Gly Gln Ala His Gln Pro Ser Val Tyr Val Leu Pro Pro Ser Arg
            340                 345                 350

Glu Glu Leu Ser Lys Asn Thr Val Ser Leu Thr Cys Leu Ile Lys Asp
        355                 360                 365

Phe Phe Pro Pro Asp Ile Asp Val Glu Trp Gln Ser Asn Gly Gln Gln
    370                 375                 380

Glu Pro Glu Ser Lys Tyr Arg Thr Thr Pro Pro Gln Leu Asp Glu Asp
385                 390                 395                 400

Gly Ser Tyr Phe Leu Tyr Ser Lys Leu Ser Val Asp Lys Ser Arg Trp
                405                 410                 415

Gln Arg Gly Asp Thr Phe Ile Cys Ala Val Met His Glu Ala Leu His
            420                 425                 430

Asn His Tyr Thr Gln Lys Ser Leu Ser His Ser Pro Gly Lys
        435                 440                 445

<210> SEQ ID NO 41
<211> LENGTH: 218
<212> TYPE: PRT
<213> ORGANISM: Artificial Sequence
<220> FEATURE:
<223> OTHER INFORMATION: canis familiaris/mus musculus

<400> SEQUENCE: 41

Asp Ala Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu His Ser
                20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
```

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr His Leu Thr Val Leu
            100                 105                 110

Gly Gln Pro Lys Ala Ser Pro Ser Val Thr Leu Phe Pro Pro Ser Ser
        115                 120                 125

Glu Glu Leu Gly Ala Asn Lys Ala Thr Leu Val Cys Leu Ile Ser Asp
    130                 135                 140

Phe Tyr Pro Ser Gly Val Thr Val Ala Trp Lys Ala Asp Gly Ser Pro
145                 150                 155                 160

Ile Thr Gln Gly Val Glu Thr Thr Lys Pro Ser Lys Gln Ser Asn Asn
                165                 170                 175

Lys Tyr Ala Ala Ser Ser Tyr Leu Ser Leu Thr Pro Asp Lys Trp Lys
            180                 185                 190

Ser His Ser Ser Phe Ser Cys Leu Val Thr His Glu Gly Ser Thr Val
        195                 200                 205

Glu Lys Lys Val Ala Pro Ala Glu Cys Ser
    210                 215

<210> SEQ ID NO 42
<211> LENGTH: 451
<212> TYPE: PRT
<213> ORGANISM: Artificial Sequence
<220> FEATURE:
<223> OTHER INFORMATION: canis familiaris/mus musculus

<400> SEQUENCE: 42

Glu Ile Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Val Tyr
65                  70                  75                  80

Met Glu Leu Arg Ser Leu Thr Ser Glu Asp Ser Ala Val Tyr Tyr Cys
                85                  90                  95

Thr Arg Asp Tyr Gly Thr Ser Gly Tyr Trp Gly Gln Gly Thr Leu Val
            100                 105                 110

Thr Val Ser Ser Ala Ser Thr Thr Ala Pro Ser Val Phe Pro Leu Ala
        115                 120                 125

Pro Ser Cys Gly Ser Gln Ser Gly Ser Thr Val Ala Leu Ala Cys Leu
    130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr 195                 200                 205
Lys Val Asp Lys Pro Val Pro Lys Arg Glu Asn Gly Arg Val Pro Arg
210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
            245                 250                 255

Arg Thr Pro Glu Val Thr Cys Val Val Val Asp Leu Asp Pro Glu Asp
                260                 265                 270

Pro Glu Val Gln Ile Ser Trp Phe Val Asp Gly Lys Gln Met Gln Thr
            275                 280                 285

Ala Lys Thr Gln Pro Arg Glu Glu Gln Phe Asn Gly Thr Tyr Arg Val
290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
            325                 330                 335

Thr Ile Ser Lys Ala Arg Gly Gln Ala His Gln Pro Ser Val Tyr Val
                340                 345                 350

Leu Pro Pro Ser Arg Glu Glu Leu Ser Lys Asn Thr Val Ser Leu Thr
            355                 360                 365

Cys Leu Ile Lys Asp Phe Phe Pro Pro Asp Ile Asp Val Glu Trp Gln
370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
            405                 410                 415

Asp Lys Ser Arg Trp Gln Arg Gly Asp Thr Phe Ile Cys Ala Val Met
                420                 425                 430

His Glu Ala Leu His Asn His Tyr Thr Gln Lys Ser Leu Ser His Ser
            435                 440                 445

Pro Gly Lys
    450

<210> SEQ ID NO 43
<211> LENGTH: 218
<212> TYPE: PRT
<213> ORGANISM: Artificial Sequence
<220> FEATURE:
<223> OTHER INFORMATION: canis familiaris/mus musculus

<400> SEQUENCE: 43

Asp Val Val Thr Gln Thr Pro Leu Ser Leu Pro Val Ser Phe Gly
1               5                   10                  15

Asp Gln Val Ser Ile Ser Cys Arg Ser Ser Gln Ser Leu Ala Asn Ser
                20                  25                  30

Tyr Gly Asn Thr Tyr Leu Ser Trp Tyr Leu His Lys Pro Gly Gln Ser
            35                  40                  45

Pro Gln Leu Leu Ile Tyr Gly Ile Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr His Leu Thr Val Leu

```
            100             105                 110
Gly Gln Pro Lys Ala Ser Pro Ser Val Thr Leu Phe Pro Pro Ser Ser
        115                 120                 125

Glu Glu Leu Gly Ala Asn Lys Ala Thr Leu Val Cys Leu Ile Ser Asp
    130                 135                 140

Phe Tyr Pro Ser Gly Val Thr Val Ala Trp Lys Ala Asp Gly Ser Pro
145                 150                 155                 160

Ile Thr Gln Gly Val Glu Thr Thr Lys Pro Ser Lys Gln Ser Asn Asn
                165                 170                 175

Lys Tyr Ala Ala Ser Ser Tyr Leu Ser Leu Thr Pro Asp Lys Trp Lys
            180                 185                 190

Ser His Ser Ser Phe Ser Cys Leu Val Thr His Glu Gly Ser Thr Val
        195                 200                 205

Glu Lys Lys Val Ala Pro Ala Glu Cys Ser
    210                 215

<210> SEQ ID NO 44
<211> LENGTH: 335
<212> TYPE: PRT
<213> ORGANISM: Felis catus

<400> SEQUENCE: 44

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ser Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Asp Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Glu
                245                 250                 255
```

Gly Phe Tyr Pro Ser Asp Ile Ala Val Glu Trp Glu Ile Thr Gly Gln
                260                 265                 270

Pro Glu Pro Glu Asn Asn Tyr Arg Thr Thr Pro Gln Leu Asp Ser
            275                 280                 285

Asp Gly Thr Tyr Phe Leu Tyr Ser Arg Leu Ser Val Asp Arg Ser Arg
        290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr His Ser Pro Gly Lys
                325                 330                 335

<210> SEQ ID NO 45
<211> LENGTH: 335
<212> TYPE: PRT
<213> ORGANISM: Felis catus

<400> SEQUENCE: 45

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ala Ser Gly Leu Tyr Ser
        50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
                100                 105                 110

Pro Lys Cys Pro Pro Pro Glu Met Leu Gly Gly Pro Ser Ile Phe Ile
            115                 120                 125

Phe Pro Pro Lys Pro Lys Asp Thr Leu Ser Ile Ser Arg Thr Pro Glu
        130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
210                 215                 220

Asp Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
            245                 250                 255

Ser Phe His Pro Pro Asp Ile Ala Val Glu Trp Glu Ile Thr Gly Gln
        260                 265                 270

Pro Glu Pro Glu Asn Asn Tyr Arg Thr Thr Pro Pro Gln Leu Asp Ser
    275                 280                 285

Asp Gly Thr Tyr Phe Val Tyr Ser Lys Leu Ser Val Asp Arg Ser His
290                 295                 300

```
<210> SEQ ID NO 46
<211> LENGTH: 110
<212> TYPE: PRT
<213> ORGANISM: Felis catus

<400> SEQUENCE: 46

Arg Ser Asp Ala Gln Pro Ser Val Phe Leu Phe Gln Pro Ser Leu Asp
 1               5                  10                  15

Glu Leu His Thr Gly Ser Ala Ser Ile Val Cys Ile Leu Asn Asp Phe
             20                  25                  30

Tyr Pro Lys Glu Val Asn Val Lys Trp Lys Val Asp Gly Val Val Gln
         35                  40                  45

Asn Lys Gly Ile Gln Glu Ser Thr Thr Glu Gln Asn Ser Lys Asp Ser
     50                  55                  60

Thr Tyr Ser Leu Ser Ser Thr Leu Thr Met Ser Ser Thr Glu Tyr Gln
65                  70                  75                  80

Ser His Glu Lys Phe Ser Cys Glu Val Thr His Lys Ser Leu Ala Ser
                 85                  90                  95

Thr Leu Val Lys Ser Phe Asn Arg Ser Glu Cys Gln Arg Glu
                100                 105                 110
```

Preceding continuation lines:
```
Trp Gln Arg Gly Asn Thr Tyr Thr Cys Ser Val Ser His Glu Ala Leu
305                 310                 315                 320

His Ser His His Thr Gln Lys Ser Leu Thr His Ser Pro Gly Lys
                325                 330                 335
```

MONOCLONAL ANTIBODIES DIRECTED TO CD20

CROSS REFERENCE TO RELATED APPLICATIONS

This application is a continuation of International Application No. PCT/US11/00415 filed Mar. 4, 2011 which claims the benefit of priority under 35 U.S.C. §119 of U.S. Provisional Application Ser. No. 61/310,440 filed Mar. 4, 2010, the contents of each are incorporated herein by reference.

FIELD OF THE INVENTION

The present invention generally relates to monoclonal antibodies, including portions or variants thereof, directed to CD20 for the treatment of diseases, e.g., in mammals and particularly in companion animals, such as dogs, cats and horses. More particularly, the invention provides antibody constructs, and antibodies encoded by the constructs, which react with CD20 and are useful for detection of targets, diagnosis of disease and treatment of companion animals. Further disclosed herein are methods for the treatment of B cell disorders in companion animals. These methods are based upon the administration of an anti-CD20 antibody or antibodies targeting the CD20 of a target animal for the modulation of B-lymphocytes.

BACKGROUND OF THE INVENTION

The use of immunoglobulins as therapeutic treatment for a variety of diseases and disorders is rapidly increasing because they have shown to be safe and efficacious therapeutic agents. Approved therapeutic monoclonal antibodies for human use include Trastuzumab (antigen: 180 kD, HER2/neu), Cetuximab (antigens: 150 kD and 170 kD, EGF receptor), Alemtuzumab (antigen: 21-28 kD, CD52), and Rituximab (antigen: 35 kD, CD20). Additional therapeutic proteins are in various phases of clinical development for use in humans for a variety of diseases with the majority targeting various forms of cancer and inflammatory-related diseases.

Whereas antibodies have been studied and developed in several mammalian species such as humans and mice, they have been significantly less studied in companion animals such as canine, feline, and equine mammals. Treatments to address veterinary immune and inflammatory conditions have been borrowed from drugs developed for humans, often with imperfect results and generally consist of drugs classified as small molecules including non-steroidal anti-inflammatory agents, analgesic agents, steroidal agents, immunosuppressive agents or anti-metabolites, and chemotherapeutic agents. The arsenal of veterinary medicine is thus limited when it comes to addressing immune conditions and cancer. Additional drawback of these treatments is that they generally only address symptoms and they are associated with serious side effects as large doses have to be administered repeatedly for a long period of time with cumulative effects that often tend to be worse than the disease itself. There is a thus a need for improved and more specific treatments and biologic agents for use in animals, such as companion animals. Heterochimeric antibodies and antibodies having enhanced effector regions for use in treating companion animals are generally and more specific treatments and biologic agents for use in animals, such as companion animals. Heterochimeric antibodies and antibodies having enhanced effector regions for use in treating companion animals are generally described in the Applicant's own international publications: US 2010/0061988A1 and US 2010/110838A2, the contents of each are incorporated herein by reference. There is still a need for highly specific antibodies which are not immunogenic in companion animals and which are effective to treat diseases characterized by over-proliferation of CD20-positive cells in companion animals.

SUMMARY OF THE INVENTION

The invention provides therapeutic antibodies useful for veterinary application, particularly antibodies directed to canine or feline or equine CD20, for example canine CD20, together with methods of making such antibodies using optimized immunogenic constructs and methods treatment using such antibodies.

DETAILED DESCRIPTION OF THE INVENTION

It is to be understood that both the foregoing general description and the following detailed description are exemplary and explanatory only and are not restrictive of the invention, as claimed. It must be noted that, as used herein and in the appended claims, the singular forms include plural referents; the use of "or" means "and/or" unless stated otherwise. Thus, for example, reference to "a subject polypeptide" includes a plurality of such polypeptides and reference to "the agent" includes reference to one or more agents and equivalents thereof known to those skilled in the art, and so forth. Moreover, it must be understood that the invention is not limited to the particular embodiments described, as such may, of course, vary. Further, the terminology used to describe particular embodiments is not intended to be limiting, since the scope of the present invention will be limited only by its claims.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Unless otherwise defined, all technical and scientific terms used herein have the same meaning as commonly understood by one of ordinary skill in the art to which this invention belongs. Suitable methods and materials are described below, however methods and materials similar or equivalent to those described herein can be used in the practice of the present invention. Thus, the materials, methods, and examples are illustrative only and not intended to be limiting. All publications, patent applications, patents, and other references mentioned herein are incorporated by reference in their entirety. In case of conflict, the present specification, including definitions, will control.

Standard techniques may be used for recombinant DNA, oligonucleotide synthesis, tissue culture and transfection (e.g., electroporation, lipofection, etc.). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989); Mayer and Walker, Immunochemical Methods In Cell And Molecular Biology, Academic Press, London (1987); Borrebaeck, Antibody Engineering, 2nd ed., Oxford Univ. Press (1995); Roitt et al., Immunology 6$^{th}$ ed., Mosby (2001); All of the references cited above, as well as all references cited herein, are incorporated herein by reference in their entireties.

The present invention provides methods for engineering heterochimeric antibodies and/or fragments thereof suitable for administration to a subject for treatment of a disease. The terms "patient," "subject," and "individual," are used interchangeably herein, to refer to mammals, including, but not limited to, humans, murines, simians, felines, canines, equines, bovines, porcines, ovines, caprines, mammalian farm and agricultural animals, mammalian sport animals, and mammalian pets. In certain embodiments of the invention, the subject is a companion animal, such as a dog, cat or horse.

Heterochimeric antibodies engineered thereof are the result of the fusion of portion of the variable domain nucleotide sequences to constant region nucleotide sequences and the co-expression of these sequences to produce heterochimeric recombinant antibodies. Furthermore, the invention relates to the use of such heterochimeric antibodies and/or fragments thereof as immunotherapeutic agents for the treatment of disease in animals and as diagnostic agents.

Heterochimeric antibodies offer several advantages, such as (i) reduced immunogenicity response upon repeated administration; (ii) increased potency mediated by an efficient recruitment of immune system responsible for effector functions in the targeted species; and (iii) increased half-life.

The present invention includes generation of antibodies and/or fragments thereof with the desired properties and their use in production. The antibodies from the present invention include a fragment of an antibody variable region derived from a species that is different than the species that contributes the constant region of the antibody. Thus, the antibodies and/or fragments thereof retain the specificities and high affinities with the desired effector functions of the target species.

The antibodies of the present invention in particular embodiments may recognize any therapeutic target suitable for antibody therapy, for example a tumor-related antigen, an allergy- or inflammation-related antigen, a cardiovascular disease-related antigen, an autoimmune disease-related antigen or a viral or bacterial infection-related antigen.

"Native antibodies" as used herein are usually glycoproteins of about 150,000 daltons, composed of two identical light chains and two identical heavy chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (variable region) ($V_H$) followed by a number of constant domains (constant regions). Each light chain has a variable domain at one end ($V_L$) and a constant domain at its other end; the constant domain of the light chain is aligned with the first constant domain of the heavy chain, and the light-chain variable domain is aligned with the variable domain of the heavy chain.

The "light chains" of antibodies from any vertebrate species can be assigned to one of two clearly distinct types, called kappa and lambda.

Depending on the amino acid sequence of the "constant domain" or "constant region" of their heavy chains, immunoglobulins can be assigned to different classes. There are five major classes of immunoglobulins: IgA, IgD, IgE, IgG, and IgM, and several of these may be further divided into "subclasses" or "isotypes", e.g., IgG1, IgG2, IgG3, IgG4, IgA, and IgA2. The heavy-chain constant domains corresponding to the different classes of immunoglobulins are called alpha, delta, epsilon, gamma, and mu, respectively.

The term "variable domain" refers to certain portions of the immunoglobulin molecule that differ in sequence among antibodies and are required for antigen binding, thereby imparting specificity to each antibody for its particular antigen. However, the variability is not evenly distributed throughout the variable domains of antibodies. It is concentrated in three segments called "hypervariable regions" both in the light chain and the heavy chain variable domains. The more highly conserved portions of variable domains are called the "framework region" (FR). The variable domains of native heavy and light chains each comprise four FRs (FR1, FR2, FR3 and FR4). The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity and complement activation.

Papain digestion of antibodies produces two identical antigen-binding fragments, called "Fab" fragments, each with a single antigen-binding site, and a residual "Fc" fragment, whose name reflects its ability to readily crystallize. Pepsin treatment yields a binding cross-linking antigen.

"Fv" as used herein, refers to the minimum antibody fragment that contains a complete antigen-recognition and binding site. This region consists of a dimer of one heavy chain and one light chain variable domain.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other configurations of antibody fragments will also be well-known to the skilled artisan.

The term "antibody" is used herein in the broadest sense and specifically includes monoclonal antibodies (including full length monoclonal antibodies), polyclonal antibodies, multispecific antibodies (e.g., bispecific antibodies), and antibody fragments exhibiting the desired biological or functional activity. The desired biological or functional activity will include at least binding to a cognate antigen and may further include complement activation and/or other effector functions. By "full length antibody" herein is meant the structure that constitutes the natural biological form of an antibody, including variable and constant regions.

"Antibody fragments" or "antigen-binding moiety" comprise a portion of a full length antibody, generally the antigen binding or variable domain thereof. Examples of antibody fragments include Fab, Fab', F(ab')$_2$, and Fv fragments; diabodies; linear antibodies; single-chain antibody molecules; and multispecific antibodies formed from antibody fragments that bind 2 or more different antigens.

The term "immunoconjugates" refers to antibodies or fragment thereof conjugated to another molecule, particularly a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different molecules, e.g., different antigens, or different epitopes on the same molecule).

The term "specificity" refers to the ability to specifically bind (e.g., immunoreact with) a given target. A polypeptide may be monospecific and contain one or more binding sites which specifically bind a target or a polypeptide may be multispecific (e.g., bispecific or trispecific) and contain two or more binding sites which specifically bind the same or different targets.

An antibody of this invention which "binds" or which "recognizes" an antigen or epitope of interest is one that binds the antigen or epitope with sufficient affinity such that the antibody is useful as a diagnostic and/or therapeutic agent in targeting the antigen. With regard to the binding of an antibody, in whole or part, to a target molecule, the term "specific binding" or "specifically binds to" or is "specific to" or is "specifically immunoreactive to" or "specifically recognizes" a particular polypeptide or an epitope on a particular polypeptide target means binding that is measurably different from a non-specific interaction. It includes reference to the preferential association of an antibody, in whole or part, with a cell or tissue bearing the CD20 target molecule and not to cells or tissues lacking that target molecule. Specific binding typically results in greater than two-fold, preferably greater than five-fold, more preferably greater than ten-fold and most preferably greater than one hundred-fold increase in amount of bound ligand to the isolated polypeptide or cell or tissue bearing CD20 as compared to a cell or tissue lacking CD20 or to a non-specific polypeptide. It is further contemplated that specific binding may be ten-fold, twenty-fold, thrity-fold, forty-fold, fifty-fold, sixty-fold, seventy-fold, eighty-fold, or ninety-fold in crease in amount of bound ligand to the isolated polypeptide or cell or tissue bearing CD20 as compared to a cell or tissue lacking CD20 or to a non-specific polypeptide. A variety of immunoassay formats are appropriate for selecting antibodies specifically immunoreactive with a particular protein. For example, ELISA immunoassays, FACS assays, Western Blots are routinely used to select monoclonal antibodies specifically immunoreactive with a protein.

An antibody binds "the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. An antibody may be said to competitively inhibit binding of the reference antibody to a given epitope by at least 90%, at least 80%, at least 70%, at least 60%, or at least 50%.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific. For example, the monoclonal antibodies to be used in accordance with the present invention may be made by the hybridoma method first described by Kohler et al., Nature 256:495 (1975), or may be made by recombinant DNA methods. The monoclonal antibodies may also be isolated e.g. from phage antibody libraries.

Monoclonal antibodies are most frequently generated in mice by administration of an "antigen" and subsequent isolation of B-cells that make antibodies. The B-cells are then immortalized by fusion to another, stable cell type of the same species as the B cell to create a "hybridoma". An individual B-cell makes one specific antibody (i.e. is clonally monospecific), which is defined by its primary amino acid sequence and its underlying gene sequence. As used herein, the terms "heterohybridoma" and "heteromyeloma" refer to lymphocyte cell lines immortalized by fusion of lymphocytes and myelomas from two different species.

Monoclonal antibodies can be initially generated, for example, by immunizing animals with an antigen or with cells that express the antigen. The generation of a hybridoma starts with the immunization of mice or companion animals such as dogs. Immunization can be performed with several types of cells in the presence or absence of adjuvants. Cells can also be used to identify the hybridoma cell lines with the desired properties by ELISA, Biacore, FACS or other methodologies available to those in the art.

Cells suitable for use in the methods of monoclonal antibody preparation according to the present invention include: (1) Peripheral Blood Mononuclear Cells (PBMC) or fractions of PBMC enriched in certain type of cells collected from healthy or diseased companion animals such as dogs, cats, or horses. Lymphocytes are pre-incubated in some instances with factors including factors including growth factors such as EPO, SCF, TNFα, TGFβ, GMCSF, TPO, IL-1, IL-2, IL-3, IL-4, GCSF to increase the expression of the antigen prior to immunization. (2) Lymphoma cell lines or tumor cell lines established from healthy or diseased subjects optionally pre-incubated with factors listed above to increase the expression of the antigen prior to immunization. (3) Cell lines derived from tissues of healthy or diseased subjects pre-incubated in some instances with factors listed above to increase the expression of the antigen prior to immunization. (4) Cultured cells engineered to express an antigen coding region or fragment thereof, such as baculovirus-infected cells, bacterial cells, yeast cells, mammalian cells, plant cells, fungal cells and the like. The antigen in the form of DNA, RNA, protein, or peptide, can be included in any one of the fractions of the cell. (5) Magnetic Proteoliposome Particles (MPLs), which are prepared from cells expressing the antigen, such that the native conformation of the transmenbrane receptor is maintained, have been described previously (see e.g., Mirzabekov et al. *Nat. Biotechnol.* 18:649-654 (2000); Babcock et al. *J. Biol. Chem.* 276:38433-38440 (2001); PCT Publication WO 01/49265; U.S. Patent Application No. 20010034432).

In certain embodiments of the invention, the generation of monoclonal antibodies can be achieved using immunogens derived from DNA, peptides, or proteins. Hybridomas are generated by immunizing an animal, which can be for example, a mouse or a companion animal, or any animal that will give a suitable antibody response. In one aspect, immunization is performed by introducing into the animal an antigen-encoding nucleic acid, or a protein antigen, such as canine CD20 or an immunogenic fragment thereof, or a nucleic acid encoding CD20 or an immunogenic fragment thereof. The skilled artisan will appreciate that certain epitopes will be more immunogenic in an animal when removed from their native environment. Thus, a peptide corresponding to an epitope of an antigen conjugated to a carrier such as keyhole limpet hemocyanin, may elicit a stronger antibody response than either the peptide alone or the epitope when part of the native protein on which it is found. Such variations and other immunization schemes are known to the skilled artisan are included in the immunization methods of the invention.

The immunogen can be a plasmid carrying a nucleic acid sequence encoding an antigen or a fragment thereof. In other embodiments of the invention, monoclonal antibodies of the invention can be obtained by screening a library of antibody molecules or fragments thereof derived from immunization of animals. Monoclonal antibodies of the invention can also be obtained from libraries of antibodies or antibody-encoding nucleic acids.

As used herein the term "antigen" is understood to be any substance capable of stimulating antibody production. Also, the term "immunogen" is understood to include any substance used to induce an immune response.

The monoclonal antibodies herein may in some embodiments include "chimeric" antibodies in which a portion of the heavy and/or light chain is identical to or homologous with corresponding sequences from antibodies derived from a particular species or belonging to a particular antibody class or subclass, while the remainder of the chain(s) is identical to or homologous with corresponding sequences in antibodies from another species or belonging to another antibody class or subclass, as well as fragments of such antibodies, exhibiting the desired biological activity (See e.g., U.S. Pat. No. 4,816,567; and Morrison et al., *Proc. Nall. Acad. Sci. USA* 81:6851-6855 (1984)).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is short to allow pairing between the two domains on the same chain, the domains are forced to pair with the complementary domains of another chain and create two antigen-binding sites.

In certain aspects the present invention provides methods for adapting antibodies to the species of an intended therapeutic target. Generally, these methods include "mammalization" which is defined as a method for transferring donor antigen-binding information to a less immunogenic mammal antibody acceptor to generate useful therapeutic treatments. More specifically, the invention provides methods for felinization, equinization and caninization of antibodies.

"Caninization" is defined as a method for transferring non-canine antigen-binding information from a donor antibody to a less immunogenic canine antibody acceptor to generate treatments useful as therapeutics in dogs.

"Felinization" is defined as a method for transferring non-feline antigen-binding information from a donor antibody to a less immunogenic feline antibody acceptor to generate treatments useful as therapeutics in cats.

"Equinization" is defined as a method for transferring non-equine antigen-binding information from a donor antibody to a less immunogenic equine antibody acceptor to generate treatments useful as therapeutics in horses.

Caninized forms of non-canine antibodies provided herein are chimeric antibodies that contain minimal sequence derived from non-canine antibodies. For the most part, caninized antibodies are canine antibody sequences ("acceptor" or "recipient" antibody) in which hypervariable region residues of the recipient are replaced by hypervariable region residues from a non-canine species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the canine antibody are replaced by corresponding non-canine FR residues. Furthermore, caninized antibodies may include residues that are not found in the recipient antibody or in the donor antibody. These modifications are made to further refine antibody performance. The caninized antibody may also comprise at least a portion of an immunoglobulin constant region (Fc) of a canine antibody.

As used herein, "identity" refers to the sequence matching between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The "percentage identity" between two sequences is a function of the number of matching positions shared by the two sequences divided by the number of positions compared-.times.100. Such alignment can be provided using, for instance, the program Basic Local Alignment Search Tool (BLAST) from the National Center for Biotechnology Information NCBI.

In one embodiment, the recombinant polypeptides, or fragments, derivatives, or modifications thereof, are specifically administered into a patient. In another embodiment, the recombinant polypeptide of the invention, or fragments, derivatives, or modifications thereof, are introduced into cells and/or a tissue while under in vitro or ex vivo conditions, prior to the transplantation of the cells and/or a tissue into a mammalian organism for the purpose of treating, preventing, reducing or otherwise lowering disease conditions or symptoms associated or mediated by the disease.

The terms "fragment" and "region" refer to portions of a polypeptide or nucleic acid molecule that contains at least 10%, 20%, 30%, 40%, 50%, 60%, 70%, 80%, 90%, 95%, or more of the entire length of the reference nucleic acid molecule or polypeptide.

The terms "polynucleotide," "nucleic acid," and "nucleic acid molecule," are used interchangeably herein to refer to polymeric forms of nucleotides of any length. The polynucleotides can contain deoxyribonucleotides, ribonucleotides, and/or their analogs. Polynucleotides can have any three-dimensional structure, and can perform any function, known or unknown. The term polynucleotide includes single-stranded, double-stranded, and triple helical molecules, and encompasses nucleic acids containing nucleotide analogs or modified backbone residues or linkages, which can be synthetic, naturally occurring, or non-naturally occurring, and which have similar binding properties as the reference nucleic acid.

"Oligonucleotide" refers generally to polynucleotides that are between 5 and about 100 nucleotides of single- or double-stranded DNA. Oligonucleotides may also refer to polynucleotides that are about 10, 20, 30, 40, 50, 60, 70, 80, or 90 nucleotides of single- or double-stranded DNA. For the purposes of this disclosure, the lower limit of the size of an oligonucleotide is two, and there is no upper limit to the length of an oligonucleotide. Oligonucleotides are also known as "oligomers" or "oligos" and can be prepared by any method known in the art including isolation from naturally-occurring polynucleotides, enzymatic synthesis and chemical synthesis.

The terms "polypeptide," "peptide" and "protein" are used interchangeably herein to refer to a polymer of amino acid residues of any length. Polypeptides can have any three-dimensional structure, and can perform any function, known or unknown. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ carboxyglutamate, and O-phosphoserine. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "conservatively modified variants" or "conservative variants" applies to both amino acid and nucleic acid sequences. With respect to particular nucleic acid sequences, conservatively modified variants refers to those nucleic acids which encode identical or substantially identical amino acid sequences; or for nucleic acids that do not encode an amino acid sequence, to nucleic acids that are substantially identical. As used herein, "substantially identical" means that two amino acid or polynucleotide sequences differ at no more than 10% of the amino acid or nucleotide positions, typically at no more than 5%, often at more than 2%, and most frequently at no more than 1% of the of the amino acid or nucleotide positions.

Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the alternate alanine codons without altering the encoded polypeptide. Such nucleic acid variations are "silent variations," which are one type of conservatively modified variants. Nucleic acid sequences encoding polypeptides described herein also encompass every possible silent variation of the nucleic acid. The skilled artisan will recognize that each amino acid codon in a nucleic acid (except AUG, which is ordinarily the only codon for methionine, and TGG, which is ordinarily the only codon for tryptophan) can be varied at one or more positions to code for the same amino acid. Accordingly, each silent variation of a nucleic acid that encodes a polypeptide is implicit in each described sequence with respect to the expression product.

"Complementarity" as applied to nucleic acids, refers to the ability of the nucleic acid to form hydrogen bond(s) with another polynucleotide sequence by either traditional Watson-Crick or other non-traditional types of base pairing. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, RNA interference, antisense or triple helix inhibition. Determination of binding free energies for nucleic acid molecules is well known in the art. "Percent complementarity" refers to the percentage of contiguous residues in a nucleic acid molecule that can form hydrogen bonds (e.g., Watson-Crick base pairing) with another nucleic acid molecule. "Perfectly complementary" or "100% complementarity" means that all the contiguous nucleotides of a nucleic acid molecule will hydrogen bond with the same number of contiguous residues in a second nucleic acid molecule. "Substantial complementarity" and "substantially complementary" as used herein indicate that two nucleic acids are at least 90% complementary, typically at least 95% complementary, often at least 98% complementary, and most frequently at least 99% complementary over a region of more than about 15 nucleotides and more often more than about 19 nucleotides.

"Homology" is an indication that two nucleotide sequences represent the same gene or a gene product thereof, and typically means that that the nucleotide sequence of two or more nucleic acid molecules are partially, substantially or completely identical. When from the same organism, homologous polynucleotides are representative of the same gene having the same chromosomal location, even though there may be individual differences between the polynucleotide sequences (such as polymorphic variants, alleles and the like). In certain embodiments, a homolog can be found in a non-native position in the genome, e.g. as the result of translocation.

The term "heterologous" refers to any two or more nucleic acid or polypeptide sequences that are not normally found in the same relationship to each other in nature. For instance, a heterologous nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion protein).

The term "homolog" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 55%, 57%, 60%, 65%, 68%, 70%, more preferably 80% or 85%, and most preferably 90%, 95%, 98%, or 99% identical at the amino acid level or nucleic acid to a reference sequence.

"Similar" sequences are those which, when aligned, share identical and similar amino acid residues, where similar residues are conservative substitutions for corresponding amino acid residues in an aligned reference sequence. In this regard, conservative residues in a sequence is a residue that is physically or functionally similar to the corresponding reference residue, e.g., that has a similar size, shape, electric charge, chemical properties, including the ability to form covalent or hydrogen bonds, or the like. The "percentage similarity" between two sequences is a function of the number of positions that contain matching residues or conservative residues shared by the two sequences divided by the number of positions compared.times.100.

"Amino acid consensus sequence" as used herein refers to a hypothetical amino acid sequence that can be generated using a matrix of at least two, and preferably more, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids. In some cases, amino acid consensus sequences correspond to a sequence or sub-sequence found in nature. In other cases, amino acid consensus sequences are not found in nature, but represent only theoretical sequences.

The amino acid sequence of a protein can be analyzed at various levels. For example, conservation or variability can be exhibited at the single residue level, multiple residue level, multiple residues with gaps etc. Residues can exhibit conservation of the identical residue or can be conserved at the class level. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Other classes are known to one of skill in the art and may be defined using structural determinations or other data to assess substitutability.

Regarding amino acid sequences, one of skill in the art will recognize that individual substitutions, deletions or insertions to a nucleic acid, peptide, polypeptide, or protein sequence which alters, inserts or deletes a single amino acid or a small percentage of amino acids in the encoded sequence is a "conservatively modified variant" where the alteration results in the substitution of an amino acid with a chemically similar amino acid. Conservative substitution tables detailing functionally similar amino acids are well known in the art. Such conservatively modified variants are in addition to and do not exclude functionally equivalent polymorphic variants, homologs, and alleles of the invention.

As used herein, when one amino acid sequence (e.g., a first VH or VL sequence) is aligned with one or more additional amino acid sequences (e.g., one or more VH or VL sequences in a database), an amino acid position in one sequence (e.g., the first VH or VL sequence) can be compared to a "corresponding position" in the one or more additional amino acid sequences. As used herein, the "corresponding position" represents the equivalent position in the sequence(s) being compared when the sequences are optimally aligned, i.e., when the sequences are aligned to achieve the highest percent identity or percent similarity.

As used herein, the term "antibody database" refers to a collection of two or more antibody amino acid sequences (a "plurality" or "multiplicity" of sequences), and typically refers to a collection of tens, hundreds or even thousands of antibody amino acid sequences. An antibody database can store amino acid sequences of, for example, a collection of antibody VH regions, antibody VL regions or both, or can store a collection of framework sequences. In one embodiment, the antibody database is a database comprising or consisting of germline antibody sequences. In another embodiment, the antibody database is a database comprising or consisting of mature antibody sequences (e.g., a Kabat database of mature antibody sequences). In another embodiment, the antibody database comprises or consists of sequences selected for one or more properties. In another embodiment, the antibody database comprises or consists of consensus sequences. In another embodiment, the antibody database comprises or consists of similar sequences. In yet another embodiment, the antibody database comprises or consists of sequences from major antibody clans (Das et al., Immunogenetics, 60:47-55 (2008); Das et al., Proc. Natl. Ac. Sci. USA. 105:16647-16652 (2008)).

As used herein, the term "property" or "characteristic" is a property of a polypeptide which is desirable and/or advantageous to one of skill in the art, e.g., in order to improve the manufacturing properties or therapeutic efficacy of the polypeptide. In one embodiment, the functional property is improved stability. In another embodiment, the functional property is improved solubility. In yet another embodiment, the functional property is non-aggregation. In still another embodiment, the functional property is an improvement in expression. In certain embodiments, the functional property is an improvement in antigen binding affinity.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "codon optimization" or "codon optimized sequences" refers to nucleotide sequences that have been optimized without altering the amino acid sequence of the original translated polypeptide and includes replacing any codons having a low usage frequency in the host species, elimination of spurious polyadenylation sequences, elimination of exon/intron splicing signals, elimination of transposon-like repeats, and optimization of GC content.

As used herein, the expressions "cell," "cell line," and "cell culture" are used interchangeably and all such designations include progeny. Thus, the words "transformants", "transfectants", "transformed cells" and "transfected cells" include the primary subject cell and cultures derived from.

Immunogenic, as used herein, refers to antigens, (including native antigens, fragments, mutant, and derivatives thereof, as well as recombinant and synthetic antigens), that, when introduced into an animal, elicit an immune response, such as a humoral or antibody response.

As used herein, the term "not immunogenic" or "non-immunogenic" means that an antigen, such as an antibody, or other molecule, does not raise an antibody response of sufficient magnitude to reduce the effectiveness of continued administration of the antibody in the majority of treated patients for sufficient time to achieve therapeutic efficacy.

As used herein, the term "therapeutic" encompasses the full spectrum of treatments for a "disease" or "disorder" or "condition". A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of a disease or disorder; or may act to minimize the time required, the occurrence or extent of any discomfort or pain, or physical limitations associated with recuperation from a disease, disorder or physical trauma; or may be used as an adjuvant to other therapies and treatments.

"Treatment," as used herein, covers any administration or application of remedies for disease in an animal, including a human, and includes inhibiting the disease, i.e., arresting its development; relieving the disease, i.e., causing its regression; and eliminating the disease, i.e., causing the removal of diseased cells or restoration of a non-diseased state. Treatment refers to both therapeutic treatment and prophylactic or preventative measures. Those in need of treatment include those already with the disorder as well as those in which the disorder is to be prevented.

A "pharmaceutical composition" or "pharmaceutically acceptable composition" of antibodies, polypeptides, or polynucleotides herein refers to a composition that usually contains a pharmaceutically acceptable carrier or excipient that is conventional in the art and which is suitable for administration into a subject for therapeutic, diagnostic, or prophylactic purposes. For example, compositions for oral administration can form solutions, suspensions, tablets, pills, capsules, sustained release formulations, oral rinses, or powders.

The term "combination therapy" refers to a therapeutic regimen that involves the provision of at least two distinct therapies to achieve an indicated therapeutic effect. For example, a combination therapy may involve the administration of two or more chemically distinct active ingredients, for example, a chemotherapeutic agent and an antibody. Alternatively, a combination therapy may involve the administration of an antibody and/or one or more chemotherapeutic agents, alone or together with the delivery of another treatment, such as radiation therapy and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending veterinarian or attending caregiver.

The term "monotherapy" refers to a treatment regimen based on the delivery of one therapeutically effective compound, whether administered as a single dose or several doses over time.

"Immune conditions" are a generic name for a wide range of diseases including arthritis, psoriasis, inflammatory bowel disease, multiple sclerosis, myocardial infarction, stroke, hemolytic anemia, atopic dermatitis, skin disorders, and the like, in which the immune system or a part thereof, such as a cell of the immune system, is abnormal or causes a disease state. Immune conditions include primary defects in an immune cell, tissue or organ, as well as "autoimmune conditions," in which the normal mechanisms for preventing immune recognition of self antigens is defective, resulting in a disease or disorder involving a non-immune cell, tissue or organ type. Cancer such as leukemias and lymphomas are primary immune disorders, while multiple sclerosis and lupus are believed to be of autoimmune origin.

A multitude of therapeutic agents have been developed over the past few decades for the treatment of various types of immune conditions for humans and these have also been used for the treatment of immune conditions in companion animals. The most commonly used types of anti-immune agents include: immunosuppressant agents (e.g., cyclosporine, thiopurine, prednisone), and analgesic and antipyretic (e.g., aspirin, ibuprofen, naproxen, celecoxib, nimesulide, licofelone, omega-3-fatty acids), each of which may be administered simultaneously, sequentially or in a common dosage regimen with antibodies of the invention.

"Cancer" as used herein, refers to any abnormal cell or tissue growth, e.g., a tumor, which can be malignant or non-malignant. Cancer is characterized by uncontrolled proliferation of cells that may or may not invade the surrounding tissue and, hence, may or may not metastasize to new body sites. Cancer encompasses carcinomas, which are cancers of epithelial cells (e.g. squamous cell carcinoma, adenocarcinoma, melanomas, and hepatomas). Cancer also encompasses sarcomas, which are tumors of mesenchymal origin, (e.g. osteogenic sarcomas, leukemias, and lymphomas). Cancers can involve one or more neoplastic cell type. Cancer a generic name for a wide range of cellular malignancies characterized by unregulated growth, lack of differentiation, and the ability to invade local tissues and metastasize. These neoplastic malignancies affect, with various degrees of prevalence, every tissue and organ in the body. A multitude of therapeutic agents have been developed over the past few decades for the treatment of various types of cancer for humans and have been used off-label or reformulated for the treatment of cancer in companion animals. The most commonly used types of anti-cancer agents include: DNA-alkylating agents (e.g., cyclophosphamide, ifosfamide), anti-metabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and immunosuppressant (e.g., prednisone), each of which may be administered simultaneously, sequentially or in a common dosage regimen with antibodies of the invention (see, for e.g., Withrow & MacEwen's, Small Animal Clinical Oncology, Saunders Elsevier, $4^{th}$ ed. (2007)).

Antibodies (mAbs) that can be subjected to the techniques set forth herein include monoclonal and polyclonal mAbs, and antibody fragments such as Fab, Fab', F(ab')2, Fd, scFv, diabodies, antibody light chains, antibody heavy chains and/or antibody fragments derived from various sources. An antibody is obtained from a sequence donor species. More particularly, the nucleic acid or amino acid sequence of the variable portion of the light chain, heavy chain or both, of the donor species antibody has specificity for a desired antigen. The donor species is any species which was used to generate the antibodies or antibody libraries, e.g., mouse, rat, rabbit, cat, dogs, goat, chicken, bovine, horse, llama, camel, dromedaries, sharks, non-human primates, human, humanized, recombinant sequence, engineered sequence, etc. Techniques for generating and cloning monoclonal antibodies are well known to those skilled in the art.

After sequencing the antibody obtained from the donor species or from a library, the variable regions (VH and VL) are separated into discrete regions such as leader sequences, frameworks (FRs) and CDRs using any published definition of CDRs and frameworks (e.g., Kabat, Chothia, AbM, contact definition and any combination thereof, and any others known to those skilled in the art). In a particular embodiment, FRs and CDRs are identified with reference to the Kabat definitions.

Whenever it appears herein, a numerical range such as "1 to 100" refers to each integer in the given range; e.g., "1 to 100 nucleotides" means that the nucleic acid can contain only 1 nucleotide, 2 nucleotides, 3 nucleotides, etc., up to and including 100 nucleotides.

With respect to the constant domains of heavy chains, a constant domain or fragment thereof of any subclass from the target species may be fused to the heavy chain heterochimeric variable domains.

The engineering of the recombinant antibody of the claimed invention can be created by introducing modifications, additions or deletions into a nucleic acid encoding the antibody by any method known in the art including recombination, error-prone PCR, shuffling, oligonucleotide-directed mutagenesis, assembly PCR, sexual PCR mutagenesis, in vivo mutagenesis, site-specific mutagenesis, gene reassembly, synthetic ligation reassembly or a combination thereof.

Further envisioned within the scope of this invention is the usage of the recombinant nucleic acids or proteins described herein, or fragments or derivatives thereof, for the treatment of all companion animal diseases and/or conditions that are mediated or associated with the onset of inflammation, as well as companion animal diseases and/or conditions that are mediated or associated with autoimmunity. Such diseases and/or conditions are referred to herein as inflammatory disorders and include but are not restricted to inflammation, autoimmune disease and immune-mediated.

In a further aspect, the invention features pharmaceutical compositions in which antibodies of the present invention are provided for therapeutic or prophylactic uses. The invention features a method for treating a dog subject having a particular antigen, e.g., one associated with disease. The method includes administering a therapeutically effective amount of a recombinant antibody specific for the particular antigen, with the recombinant antibody described herein.

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. The route of administration of the antibody or antigen-binding moiety of the invention may be oral, parenteral, by inhalation or topical. The term parenteral as used herein includes intravenous, intramuscular, subcutaneous, rectal, vaginal or intraperitoneal administration.

Antibodies produced in the manner described above, or by equivalent techniques, can be purified by a combination of affinity and size exclusion chromatography for characterization in functional biological assays. These assays include determination of specificity and binding affinity as well as effector function associated with the expressed isotype, e.g., ADCC, apoptosis, or complement fixation. Such antibodies may be used as passive or active therapeutic agents against a number of diseases, including B cell lymphoma, T cell lymphoma, autoimmune diseases, inflammatory diseases, infectious diseases, and transplantation.

"Antibody-dependent cell-mediated cytotoxicity" and "ADCC" refer to a cell-mediated reaction in which nonspecific cytotoxic cells such as Natural Killer (NK) cells, neutrophils, and macrophages recognize bound antibody on a target cell and subsequently cause lysis of the target cell (see, for e.g., Janeway et al., Immuno Biology: Elsevier Science Ltd., 4th ed., (1999)).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen.

An "enhanced" or "reduced" ADCC or CDC activity, as used herein, generally refers to a heavy chain that confers more activity or less activity than a reference heavy chain. As would be understood in the art, amount of an activity may be determined quantitatively or qualitatively in parallel or in separate runs according to any assay or technique known in the art.

In certain embodiments of the above aspects, the antigen is a tumor antigen, an antigen involved in an immune disorder, an antigen involved in an autoimmune response, a receptor expressed on a host cell or available in blood circulation or secreted by a cell and the recombinant antibody is able to either deplete undesired cells or to block or stimulates receptor functions, or neutralizes active soluble products.

The antibodies (or fragments thereof) of this invention may also be useful for treating tumors in companion animals. More specifically, they should be useful for reducing tumor size, inhibiting tumor growth and/or prolonging the survival time of tumor-bearing animals. Accordingly, this invention also relates to a method of treating tumors in a dog or other animals by administering an effective dose. An effective dose is expected to be in the range of about 0.05 to 100 milligrams per kilogram body weight per day. It is further contemplated that an effective dose may also be from about: 0.05, 0.10, 0.50, 1.0, 5.0, 10.0, 15.0, 20.0, 25.0, 30.0, 35.0, 40.0, 45.0, 50.0, 55.0, 60.0, 65.0, 70.0, 75.0, 80.0, 85.0, 90.0, 95.0 and 100 milligrams per kilogram body weight per day.

In a particular embodiment, the invention provides antibodies to CD20. The canine CD20 is a non-glycosylated integral membrane phosphoprotein expressed on the surface of almost all normal and malignant B cells. It has four membrane spanning hydrophobic regions and a short extracellular loop between the third and fourth transmembrane domain.

The CD20 protein is predicted to contain domains of amino acid sequences consisting of two extracellular domains, four transmembrane domains, and three intracellular domains as human CD20.

The amino acid sequence of canine CD20 shows sequence similarities with those of human and mice. The amino acid sequences of canine CD20 exhibit a high degree of similarity with the human gene, suggesting a similar biological function. Despite the sequence homology between the canine and human CD20 sequence, Rituximab, a monoclonal antibody to the human CD20 antigen does not react with canine B cells probably due to the lack of homology between humans and dogs in the epitope of the extracellular domain of CD20 recognized by Rituximab (Veterinary Journal, 2006, vol 171, 556). There are several reported versions of canine CD20. In one embodiment, the canine CD20 is of SEQ ID NO: 1:

MTTPRNSMSGTLPVDPMKSPTAMYPVQKIIPKRMPSVVGPTQNFFMRESK

TLGAVQIMNGLFHIALGSLLMIHTDVYAPICITMWYPLWGGIMFIISGSL

LAAADKNPRKSLVKGKMIMNSLSLFAAISGIIFLIMDIFNITISHFFKME

NLNLIKAPMPYVDIHNCDPANPSEKNSLSIQYCGSIRSVFLGVFAYMVIF

TFFQKLVTAGIVENEWKKLCSKPKSDVVVLLAAEEKKEQPIETTEEMVEL

TEIASQPKKEEDIEIIPVQEEEEELEINFAEPPQEQESSPIENDSIP

Canine antibody against the CD20 antigen expressed by normal and malignant B lymphocytes. The antibody is produced in mammalian cells (CHO or Per.C6) and meets manufacturing and purification specifications. The product is a sterile, clear, colorless, preservative free liquid concentrate for parenteral administration.

The invention thus provides: heterochimeric antibodies and/or fragments thereof that include (i) hypervariable region sequences wholly or substantially identical to sequences found in antibodies from a donor species; (ii) constant region sequences wholly or substantially identical to sequences found in antibodies from a target species which is different from the donor species; and (iii) heavy and/or light chain variable framework sequences which contain at least three contiguous non-CDR residues corresponding to sequences found in antibodies from a target species and at least three contiguous non-CDR residues corresponding to sequences found in antibodies from a donor species.

In certain embodiments antibodies of the present invention target antigens associate with a particular disease or disorder, such as acute inflammation, rheumatoid arthritis, transplant rejection, asthma, allergic inflammation, restenosis, arterial restenosis, inflammatory bowel disease, uveitis, multiple sclerosis, psoriasis, wound healing, lupus erythematosus, allergic rhinitis, atopic dermatitis, food allergies, diabetes mellitus, dermatitis, thrombotic thrombocytopenic purpura, encephalitis, leukocyte adhesion deficiency, rheumatic fever, psoriatic arthritis, osteoarthritis, ocular inflammatory disorders, progressive systemic sclerosis, primary biliary cirrhosis, CNS inflammatory disorder, antigen-antibody complex mediated diseases, autoimmune hemolytic anemia, ischemic heart disease, atherosclerosis, post-dialysis syndrome, leukemia, acquired immune deficiency syndrome, septic shock, lipid histiocytosis, and cancer.

Of particular interest is antigen CD20. The skilled artisan will appreciate that the antigen is preferably isolated or derived from the target species (e.g. canine, feline or equine), but suitable cross-reactive antibodies can in some cases be generated by using an antigen from a xenogenic species.

1.1. The antibody of any of the previous embodiments wherein the complementarity determining regions and framework regions are defined in accordance with Kabat.

1.2. The antibody of any of the previous embodiments wherein the constant region of the antibody is modified to enhance a cytotoxic effector functions selected from ADCC, antibody dependent cellular phagocytosis (ADCP), and complement dependent cytotoxicity (CDC).

In a further embodiment, the invention provides

2. Antibody 2, which is an antibody or antibody fragment that recognizes canine or feline or equine CD20, 2.1. Antibody 2 wherein the antibody is to canine or feline or equine CD20.

2.2. Antibody 2.1 wherein the antibody is derived from or has substantially the same hypervariable domain as an antibody raised against an immunogenic construct comprising or expressing a peptide containing the sequence of one or more extracellular loops of CD20.

2.3. Any of Antibodies 2-2.2 wherein the antibody induces apoptosis of cells expressing CD20.

2.4. Any of Antibodies 2-2.3 wherein the antibody suppresses growth of cells expressing CD20.

2.5. Any of Antibodies 2-2.4 wherein the antibody causes the death of cells expressing CD20 by antibody dependent cell-mediated cytotoxicity (ADCC).

2.6. Any of Antibodies 2-2.5 wherein the antibody causes the death of cells expressing CD20 by complement-dependent cytotoxicity (CDC).

2.7. Any of Antibodies 2-2.6 wherein the antibody is to feline CD20, e.g., of SEQ ID NO.:2.

2.8. Any of Antibodies 2-2.6 wherein the antibody is to canine CD20, e.g. of SEQ ID NO.:1.

2.9. Antibody 2.8 wherein the antibody is derived from or has substantially the same hypervariable domain as an antibody raised against an immunogenic construct comprising or expressing a peptide containing a sequence selected from one or more of the following sequences: SEQ ID NO.:1 and SEQ ID NO.: 2.

2.10. Antibody 2.8 or 2.9 wherein the antibody specifically recognizes an epitope on the extracellular loop of canine CD20, wherein the epitope comprises or is found within a region of the CD20 comprising or expressing a peptide containing a sequence selected from one or more of the sequences of residues 74-84, 178-188, 154-170, 140-146,162-173, 148-159, 142-153, 148-169, 166-177, or 161-176 of SEQ ID NO:1.

2.11. Any of Antibodies 2-2.6 wherein the antibody is to equine CD20.

2.12. Any of Antibodies 2-2.11 wherein the antibody comprises hypervariable sequences from a donor species antibody and constant region sequences from a target species.

2.13. Any of Antibodies 2 wherein the antibody is caninized.

2.14. Any of Antibodies 2 wherein the antibody is felinized.

2.15. Any of Antibodies 2 wherein the antibody is equinized.

2.16. Any of Antibodies 2.23 to 2.26 wherein the antibody is a heterochimeric antibody of any of Antibodies 1-1.35.

2.17. Any of Antibodies 2 wherein the antibody is monoclonal and is fully canine.

2.18. Any of Antibodies 2 wherein the antibody is monoclonal and is fully feline.

2.19. Any of Antibodies 2 wherein the antibody is monoclonal and is fully equine.

2.20. Any of Antibodies 2 recognizing a canine or feline CD20, wherein the antibody comprises a sequence selected from SEQ ID NOS 17-43.
2.21. Any of Antibodies 2 recognizing canine or feline CD20 and comprising at least one of the CDR regions from SEQ ID NOS 17-43.
2.22. Any of Antibodies 2 having the binding characteristics of an antibody selected from mAb CD20-1, CD20-2, CD20-3, CD20-4, CD20-5, and CD20-6.
2.23. Any of Antibodies 2 according to any of claims 1-3 comprising a variable domain structure selected from AVD-1 through AVD-13.
2.24. Any of Antibodies 2 comprising a light chain selected from SEQ ID NOs: 20, 21, 22, 24, 25, 26, 28, 32, 33, 36, 37, 38, 39, 41, and 43 and a heavy chain selected from SEQ ID NOs:17, 18, 19, 23, 27, 29, 30, 31, 34, 35, 38, 40, and 42.
2.25. Any of Antibodies 2 which is a heterochimeric antibody.
2.26. The antibody or antibody fragment wherein the constant domain comprises a sequence selected for providing enhanced ADCC and/or CDC.
2.27. Any of Antibodies 2 which binds to canine CD20 and wherein the constant region is of canine origin.
2.28. Any of Antibodies 2 which binds to feline CD20 and wherein the constant region is of feline origin.

The invention further provides nucleic acid encoding any of Antibodies 1 or 2.

The invention further provides a. a method of treating a patient suffering from a disease or condition characterized by the presence of abnormal cells or abnormal levels of cells expressing a target antigen comprising administering a therapeutically effective amount of an antibody binding to such target antigen, wherein the antibody is selected from Antibody 1 or 2.
b. a method of treating a patient suffering from a disease or condition characterized by the presence of abnormal cells or abnormal levels of cells expressing CD20 comprising administering a therapeutically effective amount of an antibody selected from Antibody 1 and 2.
c. Method b) wherein the patient is a dog.
d. Method c) wherein the condition to be treated is canine lymphoma.
e. Method a) wherein the disease is selected from the group consisting of: acute inflammation, rheumatoid arthritis, transplant rejection, asthma, allergic inflammation, restenosis, arterial restenosis, inflammatory bowel disease, uveitis, multiple sclerosis, psoriasis, wound healing, lupus erythematosus, allergic rhinitis, atopic dermatitis, food allergies, diabetes mellitus, dermatitis, thrombotic thrombocytopenic purpura, encephalitis, leukocyte adhesion deficiency, rheumatic fever, psoriatic arthritis, osteoarthritis, ocular inflammatory disorders, progressive systemic sclerosis, primary biliary cirrhosis, CNS inflammatory disorder, antigen-antibody complex mediated diseases, autoimmune hemolytic anemia, ischemic heart disease, atherosclerosis, post-dialysis syndrome, leukemia, acquired immune deficiency syndrome, septic shock, lipid histiocytosis, and cancer.
f. Method a, b, c or d or e further comprising administration of chemotherapy.
g. Method f wherein the chemotherapy comprises administration of one or more agents selected from cyclophosphamide, doxorubicin, vincristine, prednisone, L-asparaginase, cytoxan and adriamycin.
h. Method f or g wherein the chemotherapy spares or enhances effector cells, e.g., so as to enhance or reduce interference with ADCC effects of antibody on cancer cells.
i. Any of the foregoing methods further comprising administration of a corticosteroid, e.g., prednisone.
j. Any of the foregoing methods further comprising administration of radiation.
k. Any of the foregoing methods comprising co-administration of antibody to CD20 and CD52.

The invention further provides pharmaceutical compositions comprising any of antibodies 1 or 2, e.g., for use in any of methods a-k.

The invention further provides the use of any of antibodies 1 or 2 as pharmaceuticals, or in the manufacture of a medicament for use in any of the methods a-k.

The invention further provides a cell line stably expressing any of antibodies 1 or 2, for example a CHO cell line or PerC6 stably expressing any of antibodies 1 or 2.

The invention further provides a vector or vectors expressing at least one heavy chain and at least one light chain of any of antibodies 1 or 2.

The invention further provides a method of making an antibody comprising transforming a cell line with a vector or vectors expressing at least one heavy chain and at least one light chain of any of antibodies 1 or 2.

Antibodies to CD52, e.g. for use in Method K, are described for example in the co-pending U.S. Provisional Application Ser. No. 61/310,450, and the US and PCT applications claiming priority therefrom(now U.S. Pat. No. 8,652,470), the contents of which are incorporated herein by reference.

In another embodiment the invention provides a method of diagnosing a disease or condition treatable with the antibodies of the invention, comprising obtaining a tissue sample and measuring binding by one of the antibodies of the invention, together with diagnostic kits for performing such a method comprising an antibody of the invention, e.g., any of antibodies 1 or 2.

Thus the invention provides the following antibodies, as well as functional fragments and conservative variants thereof:

| SEQ ID NO. | Designation | Description |
| --- | --- | --- |
| SEQ ID NO. 1 | CD20 | Canine CD20 |
| SEQ ID NO. 2 | CD20 | Feline CD20 |
| SEQ ID NO. 3 | CD20 FL-F | Primer |
| SEQ ID NO. 4 | CD20 FL-R | Primer |
| SEQ ID NO. 5 | CD20 Lp-F | Primer |
| SEQ ID NO. 6 | CD20 Lp-R | Primer |
| SEQ ID NO. 7 | FCD20R | Primer |
| SEQ ID NO: 8 | VET200 | Canine HC |
| SEQ ID NO: 9 | VET201 | Canine HC |
| SEQ ID NO: 10 | VET202 | Canine HC |
| SEQ ID NO: 11 | VET203 | Canine HC |
| SEQ ID NO: 12 | VET204 | Canine HC |
| SEQ ID NO: 13 | VET205 | Canine HC |
| SEQ ID NO: 14 | VET206 | Canine HC |
| SEQ ID NO: 15 | VET100 | Canine LC |
| SEQ ID NO: 16 | VET101 | Canine LC |
| SEQ ID NO. 17 | VET256 | Mab CD20-1 HC |
| SEQ ID NO. 18 | VET229 | Mab CD20-1 HC FR4$_T$ |
| SEQ ID NO. 19 | VET230 | Mab CD20-1 HC FR1$_T$ FR4$_T$ |
| SEQ ID NO. 20 | VET132 | Mab CD20-1 LC |
| SEQ ID NO. 21 | VET119 | Mab CD20-1 LC FR4$_T$ |
| SEQ ID NO. 22 | VET120 | Mab CD20-1 LC FR1$_T$ FR4$_T$ |
| SEQ ID NO. 23 | VET259 | Mab CD20-2 HC FR4$_T$ |

-continued

| SEQ ID NO. | Designation | Description |
| --- | --- | --- |
| SEQ ID NO. 24 | VET134 | Mab CD20-2 LC |
| SEQ ID NO. 25 | VET138 | Mab CD20-2 LC FR4$_T$ |
| SEQ ID NO. 26 | VET121 | Mab CD20-3 LC FR4$_T$ |
| SEQ ID NO. 27 | VET235 | Mab CD20-4 HC FR4$_T$ |
| SEQ ID NO. 28 | VET163 | Mab CD20-3 LC |
| SEQ ID NO. 29 | VET287 | Mab CD20-4 HC |
| SEQ ID NO. 30 | VET286 | Mab CD20-5 HC |
| SEQ ID NO. 31 | VET268 | Mab CD20-5 HC FR4T |
| SEQ ID NO. 32 | VET162 | Mab CD20-5 LC |
| SEQ ID NO. 33 | VET151 | Mab CD20-5 LC FR4T |
| SEQ ID NO. 34 | VET289 | Mab CD20-6 HC |
| SEQ ID NO. 35 | VET281 | Mab CD20-6 HC FR4T |
| SEQ ID NO. 36 | VET159 | Mab CD20-6 LC |
| SEQ ID NO. 37 | VET161 | Mab CD20-6 LC FR4T |
| SEQ ID NO. 38 | VET305-Full Length HC | Mab CD20-2 HC |
| SEQ ID NO. 39 | VET305-Full Length LC | Mab CD20-2 LC |
| SEQ ID NO. 40 | VET308-Full Length HC | Mab CD20-5 HC |
| SEQ ID NO. 41 | VET308-Full Length LC | Mab CD20-5 LC |
| SEQ ID NO. 42 | VET309-Full Length HC | Mab CD20-6 HC |
| SEQ ID NO. 43 | VET309-Full Length LC | Mab CD20-6 LC |
| SEQ ID NO. 44 | VET246 | Feline HC |
| SEQ ID NO. 45 | VET249 | Feline HC |
| SEQ ID NO. 46 | VET131 | Feline LC |

Other features and advantages of the invention are apparent from the following description of the preferred embodiments thereof, and from the claims.

EXAMPLE 1

Cloning of Canine and Feline CD20

I. Cloning of Canine CD20.

The canine CD20 gene can be cloned into a mammalian expression vector and the corresponding plasmid DNA transfected into mammalian cells. Cells expressing CD20 can be used for immunization and cell-screening based assays.

CD20 are isolated from canine peripheral blood mononuclear cells (PBMC). Total RNA is extracted from 1 million canine PBMC using the MasterPureTM RNA Purification Kit (Epicentre Biotechnology). The first-strand cDNA is synthesized from 2 µg of total RNA using the First-Strand Synthesis System for RT-PCR kit (Invitrogen) according to the manufacturer's instructions. The coding region is amplified with primers of SEQ ID NO:3 and SEQ ID NO:4 and a fragment thereof encompassing the large extracellular domain (loop) are amplified with primers of SEQ ID NO:5 and SEQ ID NO:6 by PCR. The samples are denatured at 94° C. for 5 min followed by amplifications for 35 cycles (94° C. for 30 s, 62° C. for 20 s, 72° C. for 45 s) and the PCR product is sequenced.

The amino-acid sequence of the canine CD20 isolated from canine PBMC is listed as SEQ ID NO 1.

II. Cloning of Feline CD20.

The feline CD20 coding region is isolated from 5 million feline PBMC fractionated from whole blood using the Mini RNA Isolation Kit (Zymo Research). The first-strand cDNA is synthesized from 2 µl of total RNA using First-Strand Synthesis System for RT-PCR kit according to the manufacturer's instructions (Invitrogen). The coding region is then amplified by PCR using the primers of SEQ ID NO:3 and SEQ ID NO:7 using GoTaq Green Master Mix according to manufacturer's instructions. The samples are then denatured at 94° C. for 5 min followed by amplifications for 35 cycles (94° C. for 30 s, 52° C. for 30s, 72° C. for 1 min). The PCR product is cloned and sequenced.

The amino-acid sequence of the feline CD20 isolated from feline PBMC is given as SEQ ID NO:2.

EXAMPLE 2

Immunization with CD20 and Generation of Murine Monoclonal Antibodies to Canine CD20

To generate monoclonal antibodies to canine CD20, CHO-DG44 (Chinese hamster ovary cells, dihydrofolate reductase deficient ATCC CRL-9096) and NIH:3T3 (ATCC CRL-1658) are transfected with an expression vector encoding the full-length canine CD20 protein. Magnetic Proteoliposome Particles (MPLs) containing CD20, such that the native conformation of the transmenbrane receptor is maintained are prepared for immunizations and panning. In brief, recombinant canine CD20 that contains an epitope tag are solubilized from a transfected CD20-expressing cell line using the detergent CHAPSO and the protein is captured on magnetic beads via the epitope tag. A lipid membrane is reconstituted during removal of the detergent, such that the native membrane conformation of CD20 is maintained, to create the CD20-MPLs.

Anti-CD20 monoclonal antibodies are generated by immunization of mice to raise immunoglobulins specific for canine CD20. Washed CHO-DG44 cells expressing canine CD20 ($1\times10^7$ cells in 100 µL) or 100 µL of CD20-MPLs ($1\times10^9$ beads/mL) are used as immunogens. Mice are immunized with antigen in Ribi adjuvant intraperitonealy three times, then boosted twice on consecutive days. The immune response is monitored by retro-orbital bleeds. The sera are screened by FACS staining of CD20-expressing cells (versus untransfected parental cells) and CD20-MPLs.

Spleen are harvested from mice with sufficient titers of anti-CD20 immunoglobulin. A murine antibody library are prepared from spleen cells of the mice and displayed on phage such that the phage are then screened for expression of antibodies with specificity for CD20. This combination approach is generally described in U.S. Pat. No. 6,092,098 the contents of which are incorporated herein by reference.

The phage display library are screened for library members having affinity for CD20 by panning with canine CD20 incorporated into magnetic proteoliposomes (CD20-MPL). Three rounds of panning of the phage display library on the CD20-MPLs leads to several fold enrichment of CD20-binders as compared to background. Variable region fragments of interest are recloned into a Fab expression vector and the Fab retested for antigen binding against transfected CD20-expressing cells.

Anti-CD20 antibodies with high affinity for the canine CD20 exhibiting efficacy are identified by testing them in a panel of assays using methodologies available to those in the art.

The specific binding of the newly generated anti-CD20 antibodies is assessed by FACS with cells expressing CD20. Since it is important to measure the relative binding affinity of the antibodies to native CD20, live cells expressing CD20 are used in FACS analysis. For cell-binding assay, CD20 expressing cells or canine lymphoma cells are washed with phosphate-buffered saline (PBS) and seeded in wells. After one hour at room temperature to allow cell attachment to the plate surface, the cells are washed with FBS to block non-specific binding sites on the plates. Supernatants from cells expressing the anti-canine CD20 antibodies are then added. After one hour incubation at room temperature, the plates are washed with PBS. The secondary antibody is then added and detected using standard procedures.

Immunohistochemistry (IHC) is performed on lymph node tissues collected from dogs with B-cell lymphoma. Cross-sections are stained using the ImPRESS reagent (Vector Laboratories) following manufacturer's instructions. Sections are evaluated under 40× objective and scored as positive or negative compared with control tissues. B-cells and T-cells are identified by using an anti-dog CD21 antibody (Serotec) and an anti-dog CD3 antibody (Serotec), respectively. Newly generated anti-canine CD20 antibodies exhibit a strong staining of B cells and some of them with a predominant staining of the membrane.

EXAMPLE 3

Heterochimeric Antibodies

The following EXAMPLE provides general representations of heterochimeric antibodies, which are constructed according to standard techniques using the sequences and general patterns illustrated below. In the examples listed below, the CDRs are defined using the Kabat nomenclature.

I. Antibody Variable Domains.

Illustrated in Table 1, are diagrammatic representations of the heterochimerization for the light chain (AVD1 to AVD10) and heavy chain (AVD11 to AVD13) antibodies, showing contiguous sequences of discrete immunoglobulin domains. Additional antibody variants are constructed by flanking the variable regions from the donor species with any of the constant domains from the target species.

TABLE 1

| | |
|---|---|
| AVD 1: | FR1-CDR1-FR2-CDR2-FR3-CDR3-FR4$_{T\text{-}Lambda}$-C$_{T\text{-}Lambda}$ |
| AVD 2: | FR1-CDR1-FR2-CDR2-FR3-CDR3-FR4$_{T\text{-}Kappa}$-C$_{T\text{-}Lambda}$ |
| AVD 3: | FR1-CDR1-FR2-CDR2-FR3-CDR3-FR4$_{T\text{-}Lambda}$-C$_{T\text{-}Kappa}$ |
| AVD 4: | FR1-CDR1-FR2-CDR2-FR3-CDR3-FR4$_{T\text{-}kappa}$-C$_{T\text{-}Kappa}$ |
| AVD 5: | FR1$_{T\text{-}Lambda}$-CDR1-FR2-CDR2-FR3-CDR3-FR4-C$_{T\text{-}Lambda}$ |
| AVD 6: | FR1$_{T\text{-}Kappa}$-CDR1-FR2-CDR2-FR3-CDR3-FR4-C$_{T\text{-}Lambda}$ |
| AVD 7: | FR1$_{T\text{-}Lambda}$-CDR1-FR2-CDR2-FR3-CDR3-FR4-C$_{T\text{-}Kappa}$ |
| AVD 8: | FR1$_{T\text{-}kappa}$-CDR1-FR2-CDR2-FR3-CDR3-FR4-C$_{T\text{-}Kappa}$ |
| AVD 9: | FR1$_{T\text{-}Lambda}$-CDR1-FR2-CDR2-FR3-CDR3-FR4$_{T\text{-}Lambda}$-C$_{T\text{-}Lambda}$ |
| AVD 10: | FR1$_{T\text{-}kappa}$-CDR1-FR2-CDR2-FR3-CDR3-FR4$_{T\text{-}kappa}$-C$_{T\text{-}Kappa}$ |
| AVD 11: | FR1-CDR1-FR2-CDR2-FR3-CDR3-FR4$_T$-C$_T$ |
| AVD 12: | FR1$_T$-CDR1-FR2-CDR2-FR3-CDR3-FR4-C$_T$ |
| AVD 13: | FR1$_T$-CDR1-FR2-CDR2-FR3-CDR3-FR4$_T$-C$_T$ |

AVD = Antibody Variable Domain; T = Target species; Lambda = lambda light chain; Kappa = kappa light chain; C = Constant domain; FR = Framework region; CDR = Complementarity Determining Region.

II. Framework Sequences.

Exemplary framework sequences used as source to construct the light chain and heavy chain heterochimeric antibodies are generally described in the U.S. Ser. No. 12/584,390 (now U.S. Pat. No. 8,337,842) and PCT/US2009/04997 which applications are incorporated herein by reference.

III. Constant Domain Sequences.

Exemplary constant domain sequences used as a source to construct the antibody variants and/or fragments thereof are generally described in the international publication WO 2010/110838 (corresponding to U.S. Pat. No. 8,569,460), the contents of which are incorporated herein by reference.

EXAMPLE 4

Construction, Expression and Purification of Antibody Variants

The anti-CD20 monoclonal antibodies are generated in a non-canine mammal and may not be suitable for repeated administration. Antibody variants are generated to include sequences from the target species. The antibody variants are then tested for a panel of properties.

I. Antibody Variants Derived from the Mouse Anti-canine CD20 Antibodies.

The mouse anti-dog CD20 antibodies are modified as described in EXAMPLE 3. Variable regions are prepared by assembling synthetic oligonucleotides and cloned into pSMART with HindIII and NheI as flanking restriction sites on the 5'- and 3'- end of the variable domains, respectively. Assembled products are then subcloned into an expression vector containing a promoter and the heavy chain constant domain or containing the lambda light chain constant domain. The entire expression cassette includes the human cytomegalovirus immediate-early (CMV) promoter, a kozak sequence and signal peptide sequence immediately upstream of the coding sequence and in frame with the variable region of both the light and heavy chains to direct the resulting antibody product towards the secretory pathway. The vectors also contain a lambda canine light chain constant domain and a canine heavy chain constant domain.

II. Expression, Purification and Quantitation of Antibody Variants.

These plasmids are transformed into *E. coli* chemically competent *E. coli* cells (Lucigen), grown in Luria Broth (LB) media and stocked in glycerol. Large scale plasmid DNA are prepared as described by the manufacturer (Zymo Research Corp.). The antibody variants are transiently expressed in the human embryonic kidney cell line 293F (Invitrogen) in serum-free condition. The heavy chain (VET200 series) and light chain (VET100 series) expression vectors are co-transfected using 293fectin (Invitrogen) and grown in 293F-FreeStyle culture medium (Invitrogen). The transfected 293 cultures expressed approximately 5-20 mg/L of recombinant antibody. Binding assays are performed with supernatants or with recombinant antibodies purified from supernatants.

The antibody titer is determined using a quantitative ELISA. Plates are coated with 100 μL/well at 37° C. for 1 hour with rabbit anti-dog IgG (H+L) antibody (Jackson Immuno-Research) diluted 1:100 in carbonate buffer (100mM NaHCO$_3$, 33.6 mM Na$_2$CO$_3$, pH 9.5). The plates are washed three times with TBS-T (50mM Tris, 0.14 M NaCl, 0.05% tween-20, pH 8.0) and blocked with 200 μL/well TBS/BSA (50mM Tris, 0.14 M NaCl, 1% BSA, pH 8.0) for 1 hour at 37° C. The standard is prepared by diluting the reference antibody (Jackson Immuno-Research, Dog Gamma Globulin 10.0 mg) in TBS-T/BSA (TBS-T, 1% BSA) in a range of concentration from 0 to 500 ng/ml. After washing the plates twice with TBS-T, standard/samples preparation are added to each well and incubated at 37° C. for 1 hour. The plates are then washed 3× with TBS-T and incubated for 1 hour at 37° C. with HRP-rabbit anti-dog IgG antibody (Perodixase Rabbit Anti-Dog IgG (H+L) Jackson Immuno-Research) diluted 1:20,000 in TBS-T/BSA. The plates are washed twice with TBS-T and developed using 100 gL/well of TMB substrate. The reaction is stopped with 1 M H$_2$SO$_4$ and the OD is measured at 450 nm. The standard curve is fitted using a four parameter equation and used to calculate the antibody concentration in the samples.

Antibodies are purified from culture supernatants using protein A affinity chromatography. Supernatants are diluted 1:1 with Binding Buffer (Pierce) and passed over a gravity-flow column (GE Healthcare), equilibrated with 20 resin-bed volumes of Binding Buffer. The antibody retained on the column is washed with 15 ml of binding buffer, eluted with low pH elution buffer (Pierce) and collected in 1 ml fractions containing 100 μL, of Binding Buffer to neutralize the pH. Fractions with absorbance (280 nm)>0.1 are desalted using desalting columns (Pierce).

III. Anti-canine CD20 Antibody Variant Sequences.

The amino-acid sequence of the isolated antibody and the antibody variants is given as SEQ ID NO.:17 to SEQ ID NO.:43

IV. Designation of Anti-canine CD20 Antibody Variant Sequences.

Table 2 summarizes the designation and the parts of the various vectors.

TABLE 2

| Designation | Variable Domain | Constant Domain |
|---|---|---|
| VET124 | VET121 | VET101 |
| VET133 | VET132 | VET101 |
| VET135 | VET134 | VET101 |
| VET237 | VET235 | VET201 |
| VET257 | VET256 | VET201 |
| VET258 | VET256 | VET205 |
| VET260 | VET259 | VET201 |

EXAMPLE 4

Binding of Antibody Variants to Cells

I. Antibody Variants to CD20 Bind Canine PBMCs.

In the present example, the antibody variants are incubated with the CD20 positive cells and the amount of bound antibody is assessed following incubation with a fluorescent-labeled reporter reagent. The reporter is thereafter measured by FACS.

Briefly, for each assay, one million cells of Peripheral Blood Mononuclear Cell (PBMC) isolated from whole blood from a normal dog by standard techniques were resuspended in FACS buffer (PBS+2% FBS). Two μg of the primary antibody are added to the cells and the samples were incubated at 4° C. for 1 h. The primary antibody is provided as supernatants from transfected cells with recombinant antibody constructs or from purified antibody preparation. The mouse anti-dog CD21 mAb (Serotec) recognizing B-lymphocytes is added to the cells as a control to estimate the percentage of B-lymphocytes in a given sample. One ml of FACS buffer are added and cells are spun down for 3 min at 800× g in Eppendorf microcentrifuge. The cells are washed with 1 mL FACS buffer and spun down again. The secondary antibodies such as fluorescein-isothiocynate (FITC) conjugated goat anti-mouse kappa (mFITC, Jackson ImmunoResearch), or the FITC-conjugated goat anti-dog IgG (H+L) (dFITC, Bethyl Laboratories) are added in 100 μL of FACS buffer supplemented with 1% BSA to appropriate tubes and the tubes were incubated at 4° C. for 30 minutes. The wash steps are repeated. The cells are then resuspended in 500 μL FACS buffer and transferred into 12×75 mm polystyrene test tubes. The cells are analyzed by FACS with a FacScan cytometer using the CellQuest software (Becton-Dickenson). Analysis gates are set on the live lymphocyte population based on typical forward and side scatter characteristics. Several controls are utilized to determine the background fluorescence: (i) one tube of cells is incubated with the FITC-conjugated secondary antibody without the primary antibody, and (ii) one tube of cells is incubated with PBS only.

A typical staining profile is reported in Table 3. The overall percentage of B-cell subset in this sample is estimated to be approximately 12% based on the binding of the anti-dog CD21 mab control. The results of Table 3 evidence effective binding of the antibody variants to lymphocytes.

TABLE 3

Binding of antibody variants to canine PBMCs.

| | % Lymphocytes | Mean Fluorescence |
|---|---|---|
| PBMC | 0.37 | 31.56 |
| PBMC + dFITC | 0.47 | 43.86 |
| PBMC + VET 133 X VET 257 + dFITC | 12.03 | 3165.67 |
| PBMC + VET 135 X VET 257 + dFITC | 8.33 | 2499.17 |
| PBMC + VET 133 X VET 260 + dFITC | 13.73 | 2906.29 |
| PBMC + VET 135 X VET 260 + dFITC | 12.72 | 2659.34 |
| PBMC + VET 124 X VET 237 + dFITC | 13.00 | 2656.60 |

II. Antibody Variants to CD20 Bind Cells Expressing Feline CD20.

The binding of the antibody variants of the present invention raised to canine CD20 can be assessed by FACS analysis for their binding to feline CD20 according to standard immunological techniques (see Veterinary Immunology and Immunopathology 2005, 106:179-196; Brousseau et al., Manual of Immunology Methods, CRC Press, 1998).

In the present example, the antibody variants (2.5 μg/mL) are incubated with mammalian cells expressing the recombinant feline CD20 or canine CD20 or control cells. The amount of bound antibody is assessed by detection with a fluorescent-labeled reporter antibody reagent. Several controls are utilized to determine the background fluorescence: (i) CD20 expressing cells are incubated with the conjugated secondary antibody with an isotype antibody, and (ii) Control cells are incubated with the anti-CD20 antibodies.

A typical binding profile is reported in Table 4. The results reported as mean fluorescence units evidence effective binding of the antibodies CD20-2, CD20-5, and CD20-6 to the recombinant canine CD20 expressed in HEK cells. Only CD20-2 and CD20-5 antibodies bind feline CD20 expressed in mammalian cells.

TABLE 4

| Mab | Canine CD20 | Feline CD20 | Control Cells |
|---|---|---|---|
| CD20-2 | 2340 | 2209 | 49 |
| CD20-5 | 2769 | 2048 | 215 |
| CD20-6 | 2107 | 60 | 4 |
| Isotype | 55 | 50 | 14 |

III. Anti-CD20 Antibody Variants Alter Proliferation of Tumor Cells.

The antibody variants of the present invention were tested for their ability to alter proliferation of lymphoma cells.

Lymphoma cells are grown in RPMI medium with FBS 10% in 5% carbon dioxide ($CO_2$) at 37° C. Cells are seeded at 5,000 cells/well in 96-well plates in medium with 5% FBS. Cells are treated with the antibody variants or isotype controls (10 μg/ml) and incubated for 72 h at 37° C. in a $CO_2$ incubator. Ten (10) μL, MTT solution is added to each well and incubated at 37° C. for 4 h according to the manufacturer's instruction (Trevigen). Optical density (OD) is then measured at 490 nm and data is presented as percentage of reduction of cell proliferation of triplicate measurements. The data in Table 5 illustrate that the antibody variants have an anti-proliferative effect on lymphoma cells. Furthermore, the antibody variants sensitize the lymphoma cell line to Doxorubicin, a cytotoxic drug commonly used in the treatment of cancer for companion animals.

TABLE 5

Effects of antibody variants on proliferation of lymphoma cells.

| Mabs (10 ug/mL) | Doxorubicin | | |
|---|---|---|---|
| | 0 nM | 6.6 nM | 66 nM |
| Isotype Control | −0.30 | 12.20 | 38.69 |
| VET 133 X VET 257 | 59.82 | 65.77 | 76.79 |
| VET 135 X VET 260 | 40.48 | 58.63 | 64.88 |

The antibody variants of the present invention are further tested for their ability to alter proliferation of lymphoma cells. Cell assays are conducted as described in the example above. Data is presented in Table 6 as percentage of reduction of cell proliferation of triplicate measurements. The data illustrate that the antibody variants at a concentration of 10 µg/mL with various affinities exhibit various level of anti-proliferative effect on lymphoma cells.

TABLE 6

Effects of antibody variants on proliferation of lymphoma cells.

| Mabs | Reduction (%) | KD (nM) |
|---|---|---|
| CD20-2 (VET305) | 55.0 | 8.845 |
| CD20-3 | 22.4 | 76.28 |
| CD20-4 | 17.5 | 77.37 |
| CD20-5 (VET308) | 60.1 | 1.21 |
| CD20-6 (VET309) | 27.6 | 63.41 |

IV. Affinity and Epitope of Anti-CD20 Antibody Variants.

The antibody variants of the present invention are compared for their binding affinity to canine CD20. Binding affinity is assessed by measuring binding to the recombinant canine CD20 expressed in CHO cells by FACS analysis as described above. The affinity is 1.0 nM, 8.845 nM, 76.28 nM, 77.37 nM, 1.2 nM, 63.41 nM for the anti-canine CD20 antibodies CD20-1, CD20-2, CD20-3, CD20-4, CD20-5, and CD20-6, respectively.

Competition experiments are performed using standard techniques. Briefly, biotinylated recombinant anti-canine CD20 antibodies are titrated on CHO cells expressing recombinant canine CD20. Cells are first incubated with an excess of unlabelled recombinant anti-canine CD20 antibody (25 µg/mL). Thereafter, cells are incubated with a biotin-labeled antibody at 2 µg/mL. After washing, cells are incubated with streptavidin- phycoerythrin and fluorescence is analyzed by flow cytometry. An irrelevant antibody is used as negative control for inhibition. Results are expressed as a ratio between fluorescence intensity of the cells pre-incubated with the unlabelled antibody and the fluorescence intensity obtained for each biotinylated antibody alone. The percentage of inhibition (PI) is calculated by the following formula: PI=[1−(Experimental−Background)/Biotinylated antibody alone−Background)]×100%.

The results reported in Table 7 evidence that antibody CD20-1, CD20-3, and CD20-6 recognize different epitopes of canine CD20.

TABLE 7

Epitope mapping of anti-CD20 antibody variants using CHO cells expressing the recombinant canine CD20.

| Competitor mab | Labeled Antibody (2 µg/mL) | | |
|---|---|---|---|
| | CD20-1 | CD20-2 | CD20-5 |
| CD20-1 | 111.65 | −22.08 | 87.68 |
| CD20-2 | 0.90 | 124.33 | 3.69 |
| CD20-5 | 107.07 | 6.47 | 85.88 |
| CD20-6 | 6.03 | 1.41 | 5.99 |

V. Creation of Anti-CD20 Producing Cell Line

The vectors harboring both the light chain gene and the heavy chain gene of the anti-canine CD20 antibody CD20-2 and CD20-5 are introduced into mammalian cells to create a cell line expressing the corresponding recombinant antibody. In this example, PER.C6 cells are used as mammalian cells. Cells are cultured in a chemically-defined, protein-free medium CDM4PerMab (Hyclone, Thermo-Scientific, Cat No. SH30871.02) supplemented with 3.0 mM Glutamine (Invitrogen, Gibco, Cat No. 25030-081). Four passages after thaw, the PER.C6 cells are transfected by electroporation using standard techniques with the linearized vector DNA. Cells which stably incorporate the vector are selected for by survival in the presence of 125.0 ug/mL Geneticin (Invitrogen, Cat No. 11811-023) by limited dilution at a seeding density of 0.3 cells per well in 96-well plates. When colonies became visible, single clones from single wells are first measured for titer and binding to the target and then scaled-up to larger wells. Selected clones are further evaluated in larger scale cultures for antibody titer, binding to CD20-expressing cells, cell doubling time, cell viability, and cell stability. Clones with optimal characteristics are frozen in the culture medium supplemented with 7.5±0.5% Dimethylsulphoxide (Sigma, Cat No. D2650).

VI. Half-life of the recombinant anti-canine CD20

The half-life of the recombinant anti-canine CD20 antibody are assessed. In this example, the half-life of antibody CD20-2 (VET305) is assessed by dosing beagle dogs intravenously. Blood is collected for analysis of CD20-2 in plasma samples harvested as whole blood treated with Ethylenediaminetetraacetic acid (EDTA) as the anticoagulant. An enzyme linked immunosorbant assay (ELISA) method is utilized to determine the plasma antibody concentrations. In this assay, a 96-well plate is coated with a rabbit polyclonal antibody raised to the variable domain of the antibody CD20-2. The antibody CD20-2 in standards or in samples is captured by the polyclonal antibody and is detected by an enzyme conjugated anti-dog secondary antibody. A non-linear regression fit of the standards is used to determine the recombinant antibody concentrations in plasma.

A single dose of 2.4 mg/kg of the antibody CD20-2 shows that high plasma antibody concentrations are achieved in all animals and that its elimination half-life ranges between 56 to 67 hours. Multiple doses of the antibody CD20-2 ranging from 2.0 to 5.0 mg/kg show that plasma antibody concentrations increases overtime and persists at significant levels during the treatment intervals with elimination half life of longer than one week and the volume of distribution approximating plasma volume.

Interestingly, the half-life values of the antibody CD20-2 increase after consecutive administration. The half-life values are influenced by the number of target cells and depend on the size of the B lymphocyte pool at a given time point. Due to the binding to CD20 and eventual lysis of lymphocyte cells, the B-cell depleting effect of the antibody could explain half-life value increases.

VII. Depletion of B Cells in Vivo

Three beagle dogs receive three consecutive dosages of the antibody CD20-2 (VET305) ranging from 2.0 mg/kg to 5.0 mg/kg every 5 days. Blood samples drawn at several time points are centrifuged at 2000 RPM for 5 min. Plasma is removed for assay of the antibody levels. The pellet containing peripheral blood leukocytes and red blood cells is resuspended in a plasma equivalent volume of phosphate saline solution (Dulbecco's Phosphate-Buffered Saline, Mediatech, Cat No. 21-030-CM) for quantitation of lymphocyte populations by flow cytometry. A 0.1 mL volume of the cell preparation is distributed into micro-centrifuge tubes. Labeled monoclonal antibody with specificity for the canine lymphocyte surface marker CD21 is added to the vial to identify the B lymphocyte cell population. An additional sample is included with no reagents for determination of autofluorescence. Cells are incubated with the fluorescent antibody for 30 min. Red blood cell were then lyzed for 15 min using a lysis buffer (Red Blood Cell Lysis Buffer, Biolegend,Cat No. 420301) and then washed prior to analysis on a Becton Dickinson FACS instrument.

Interestingly, a single dose of 2.4 mg/kg of the antibody CD20-2 trigger a rapid and sustained B-cell depletion ranging from 36 to 95% of the pre-dosing level. Three consecutive doses of 2.4 mg/kg to 5.0 mg/kg of the antibody CD20-2 show a decrease in-B lymphocyte cell percentage after treatment across all tested dose ranges and depletion is maintained for at least 10 days after the last dose.

Weekly dose of the antibody CD20-2 over a period of 4 weeks is well tolerated locally and systemically and no adverse effects are noticed on clinical and behavioral observations or body weights.

EXAMPLE 5

Treatment with Anti-CD20 Antibody Variants

I. Treatment of Dogs.

A dog diagnosed with an immune condition including lymphoma, relapsed lymphoma, leukemia, mast cell tumor, hemolytic anemia, arthritis, atopic dermatitis is given therapy with the anti-CD20 monoclonal antibody. The dog is infused intravenously or subcutaneously with 1-5 mg/kg of antibody, and the treatment is repeated weekly for 4-8 weeks following the initial treatment. Two months after the final dose, the patient shows reduced levels of certain types of cells expressing CD20. The dog is then treated under a maintenance regimen with administration of the anti-CD20 antibody every 8-12 weeks. It is contemplated that a dog may be infused intravenously, subcutaneously, intramuscularly, or intraperitoneally. It is contemplated that a dog may be dosed at 1.0, 1.5, 2.0, 2.5, 3.0, 3.5, 4.0, 4.5 or 5 mg/kg of antibody. It is contemplated that a dog may be given antibody at doses lower than 1 mg/kg of body weight.

II. Treatment of Arthritis.

A dog with confirmed arthritis receives 1 mg/kg of anti-CD20 antibody treatment alone or in combination with standard treatment of care two to three times a week for an initial four weeks. Clinical response to treatment is assessed for improvement at the study end point. Improvement is defined as one of the following: (i) Reduction of at least 1 grade in lameness score at a walk or trot, and/or (ii) A combined reduction of at least 2 grades in scores for pain on palpation or manipulation, range of joint motion, and joint swelling. Overall lameness, pain on palpation or manipulation, range of motion, and joint swelling are observed at the scheduled times and scored as follows: (i) Overall Lameness Scoring (scored at a walk and a trot)[0=No lameness, 1=Mild lameness (dog touched toe to floor on all strides), 2=Moderate lameness (dog touched toe to floor on all strides), 3=Severe lameness (dog touched toe to floor on at least 50% of strides), 4=Non-weight bearing lameness (dog touched toe to floor on less than 50% of strides)]; (ii) Pain on Palpation/Manipulation (most severely affected limb) [0=No pain or not applicable, 1=Slightly painful (scarcely withdrew limb), 2=Moderately painful (definitely withdrew limb), 3=Severely painful (prominently withdrew limb)]; (iii) Range of Motion (most severely affected limb) [0=Normal range of motion, 1=Slightly reduced (less than 25% reduction in range), 2=Moderately reduced (25% to 50% reduction in range), 3=Severely reduced (greater than 50% reduction in range)]; and (iv) Joint Swelling (most severely affected limb) [0=No swelling or not applicable, 1=Mild swelling (fibrosis or mild, palpable fluid distension), 2=Moderate swelling (obvious, palpable fluctuant fluid distension), 3=Severe swelling (pronounced, palpable fluctuant fluid distension)]. Two months after the final dose, the patient shows overall improvement. The dog is then treated under a maintenance regimen with administration of the anti-CD20 antibody every 8-12 weeks.

III. Treatment of Cats.

A cat diagnosed with an immune condition including lymphoma, relapsed lymphoma, leukemia, mast cell tumor, hemolytic anemia, arthritis, atopic dermatitis is given therapy with the anti-CD20 monoclonal antibody. The cat is infused intravenously or subcutaneously with 1-5 mg/kg of antibody, and the treatment is repeated weekly for 4-8 weeks following the initial treatment. Two months after the final dose, the patient shows reduced levels of certain types of cells expressing CD20. The cat is then treated under a maintenance regimen with administration of the anti-CD20 antibody every 8-12 weeks. It is contemplated that a cat may be infused intravenously, subcutaneously, intramuscularly, or intraperitoneally. It is contemplated that a cat may be dosed at 1.0, 1.5, 2.0, 2.5, 3.0, 3.5, 4.0, 4.5 or 5 mg/kg of antibody. It is contemplated that a cat may be given antibody at doses lower than 1 mg/kg of body weight.

Alternative combinations and variations of the examples provided will become apparent based on this disclosure. It is not possible to provide specific examples for all of the many possible combinations and variations of the embodiments described, but such combinations and variations are nevertheless intended to be within the scope of the invention.

SEQUENCE LISTING

| SEQ ID NO. | Sequence |
|---|---|
| SEQ ID NO. 1 | MTTPRNSMSGTLPVDPMKSPTAMYPVQKIIPKRMPSVVGPTQNFFMRESKTLGAVQIMNGLFH IALGSLLMIHTDVYAPICITMWYPLWGGIMFIISGSLLAAADKNPRKSLVKGKMIMNSLSLFA AISGIIFLIMDIFNITISHFFKMENLNLIKAPMPYVDIHNCDPANPSEKNSLSIQYCGSIRSV FLGVFAVMVIFTFFQKLVTAGIVENEWKKLCSKPKSDVVVLLAAEEKKEQPIETTEEMVELTE IASQPKKEEDIEIIPVQEEEEELEINFAEPPQEQESSPIENDSIP |

SEQUENCE LISTING

| SEQ ID NO. | Sequence |
| --- | --- |
| SEQ ID NO. 2 | MTTPRNSMSGTLPADAMKSPTAMNPVQKIIPKKMPSVVGPTQNFFMKESKPLGAVQIMNGLFH<br>MALGGLLMIHMEVYAPICMTVWYPLWGGIMYIISGSLLVAAEKNPRKSLVKGKMIMNSLSLFA<br>AISGMILLIMDIFNIAISHFFKMENLNLLKSPKPYIDIHTCQPESKPSEKNSLSIKYCDSIRS<br>VFLSIFAVMVVFTLFQKLVTAGIVENEWKKLCSKPKADVVVLLAAEEKKEQLVEITEEAVELT<br>EVSSQPKNEEDIEIIPVQEEEEETEMNFPEPPQDQEPSLIENDSIP |
| SEQ ID NO. 3 | 5'-TGAGATGACAACACCCAGAAA-3' |
| SEQ ID NO. 4 | 5'-TTAAGGGATGCTGTCGTTTTC-3' |
| SEQ ID NO, 5 | 5'-AATATTACCATTTCCCATTTTTTA-3' |
| SEQ ID NO. 6 | 5'-TATGCTGCCACAATATTGTATAG-3' |
| SEQ ID NO. 7 | 5'-GGATCCTTAAGGAATGCTATCGTTTT-3' |
| SEQ ID NO. 8 | ASTTAPSVFPPLAPSCGSQSGSTVALACLVSGYIPEPVTVSWNSGSLTSGVHTFPSILQSSGLY<br>SLSSMVTVPSSRWPSETFTCNVAHPATNTKVDKPVVKECECKCNCNNCPCPGCGLLGGPSVFI<br>FPPKPKDILVTARTPTVTCVVVDLDPENPEVQISWFVDSKQVQTANTQPREEQSNGTYRVVSV<br>LPIGHQDWLSGKQFKCKVNNKALPSPIEEIISKTPGQAHQPNVYVLPPSRDEMSKNTVTLTCL<br>VKDFFPPEIDVEWQSNGQQEPESKYRMTPPQLDEDGSYFLYSKLSVDKSRWQRGDTFICAVMH<br>EALHNHYTQKSLSHSPGK |
| SEQ ID NO:9 | ASTTAPSVFPPLAPSCGSQSGSTVALACLVSGYFPEPVTVSWNSGSLTSGVHTFPSVLQSSGLY<br>SLSSMVTVPSSRWPSETFTCNVAHPASKTKVDKPVPKRENGRVPRPPDCPKCPAPEMLGGPSV<br>FIFPPKPKDTLLIARTPEVTCVVVDLDPEDPEVQISWFVDGKQMQTAKTQPREEQFNGTYRVV<br>SVLPIGHQDWLKGKQFTCKVNNKALPSPIERTISKARGQAHQPSVYVLPPSREELSKNTVSLT<br>CLIKDFFPPDIDVEWQSNGQQEPESKYRTTPPQLDEDGSYFLYSKLSVDKSRWQRGDTFICAV<br>MHEALHNHYTQKSLSHSPGK |
| SEQ ID NO: 10 | ASTTAPSVFPPLAPSCGSTSGSTVALACLVSGYFPEPVTVSWNSGSLTSGVHTFPSVLQSSGLY<br>SLSSMVTVPSSRWPSETFTCNVAHPASKTKVDKPVPKRENGRVPRPPDCPKCPAPEMLGGPSV<br>FIFPPKPKDTLLIARTPEVTCVVVDLDPEDPEVQISWFVDGKQMQTAKTQPREEQFNGTYRVV<br>SVLPIGHQDWLKGKQFTCKVNNKALPSPIERTISKARGQAHQPSVYVLPPSREELSKNTVSLT<br>CLIKDFFPPDIDVEWQSNGQQEPESKYRTTPPQLDEDGSYFLYSKLSVDKSRWQRGDTFICAV<br>MHEALHNHYTQKSLSHSPGK |
| SEQ ID NO: 11 | ASTTAPSVFPPLAPSCGSQSGSTVALACLVSGYFPEPVTVSWNSGSLTSGVHTFPSVLQSSGLY<br>SLSSMVTVPSSRWPSETFTCNVAHPASKTKVDKPVPKRENGRVPRPPDCPKCPAPEMLGGPSV<br>FIFPPKPKDTLLIARTPEVTCVVVDLDPEDPEVQISWFVDGKQMQTAKTQPREEQFNGTYRVV<br>SVLPIGHQDWLKGKQFTCKVNNKALPSPIERTISKARGQAHQPSVYVLPPSREELSKNTVSLT<br>CLIKDFFPPDIDVEWQSNGQQEPESKYRTTPPQLDEDGSYFLYSKLSVDKSRWQRGDTFICAV<br>MHEALHNHYTQKSLSHSPGK |
| SEQ ID NO: 12 | ASTTAPSVFPPLAPSCGSTSGSTVALACLVSGYFPEPVTVSWNSGSLTSGVHTFPSVLQSSGLY<br>SLSSMVTVPSSRWPSETFTCNVAHPASKTKVDKPVPKRENGRVPRPPDCPKCPAPEMLGGPSV<br>FIFPPKPKDTLLIARTPEVTCVVVDLDPEDPEVQISWFVDGKQMQTAKTQPREEQFNGTYRVV<br>SVLPIGHQDWLKGKQFTCKVNNKALPSPIERTISKARGQAHQPSVYVLPPSREELSKNTVSLT<br>CLIKDFFPPDIDVEWQSNGQQEPESKYRTTPPQLDEDGSYFLYSKLSVDKSRWQRGDTFICAV<br>MHEALHNHYTQKSLSHSPGK |
| SEQ ID NO: 13 | ASTTAPSVFPPLAPSCGSQSGSTVALACLVSGYIPEPVTVSWNSGSLTSGVHTFPSILQSSGLY<br>SLSSMVTVPSSRWPSETFTCNVAHPATNTKVDKPVVKECECKCNCNNCPCPGCGLLGGPSVFI<br>FPPKPKDILVTARTPTVTCVVVDLDPENPEVQISWFVDGKQMQTAKTQPREEQFNGTYRVVSV<br>LPIGHQDWLKGKQFTCKVNNKALPSPIERTISKARGQAHQPSVYVLPPSREELSKNTVSLTCL<br>IKDFFPPDIDVEWQSNGQQEPESKYRTTPPQLDEDGSYFLYSKLSVDKSRWQRGDTFICAVMH<br>ESLHNHYTQKSLSHSPGK |
| SEQ ID NO: 14 | ASTTAPSVFPPLAPSCGSTSGSTVALACLVSGYFPEPVTVSWNSGSLTSGVHTYPSVLQSSGLY<br>SLSSMVTVPSSRWPSETFTCNVAHPASKTKVDKPVPKRENGRVPRPPGCPKCPAPEMLGGPSV<br>FIFPPKPKDTLLIARTPEVTCVVVDLDPEDPEVQISWFVDSKQVQTANTQPREEQSNGTYRVV<br>SVLPIGHQDWLSGKQFKCKVNNKALPSPIEEIISKTPGQAHQPNVYVLPPSRDEMSKNTVTLT<br>CLVKDFFPPEIDVEWQSNGQQEPESKYRMTPPQLDEDGSYFLYSKLSVDKSRWQRGDTFICAV<br>MHEALHNHYTQKSLSHSPGK |
| SEQ ID NO: 15 | NDAQPAVYLFQPSPDQLHTGSASVVCLLNSFYPKDINVKWKVDGVIQDTGIQESVTEQDKDST<br>YSLSSTLTMSSTEYLSHELYSCEITHKSLPSTLIKSFQRSECQRVD |
| SEQ ID NO: 16 | GQPKASPSVTLFPPSSEELGANKATLVCLISDFYPSGVTVAWKADGSPITQGVETTKPSKQSN<br>NKYAASSYLSLTPDKWKSHSSFSCLVTHEGSTVEKKVAPAECS |
| SEQ ID NO: 17 | EIQLQQSGAELVKPGASVKISCKASGYTFTDYYINWVKQRPGQGLEWIGKIGPGSGRTYYNEK<br>FKGKATLTADKSSSTAYIQSSLTSEDSAVYFCAVLSWGQGTTLTVSS |

SEQUENCE LISTING

| SEQ ID NO. | Sequence |
| --- | --- |
| SEQ ID NO. 18 | EIQLQQSGAELVKPGASVKISCKASGYTFTDYYINWVKQRPGQGLEWIGKIGPGSGRTYYNEK<br>FKGKATLTADKSSTAYIQISSLTSEDSAVYFCAVLSWGQGTLVTVSS |
| SEQ ID NO. 19 | EVQLVESGGDLVKPGGSLRLSCKASGYTFTDYYINWVKQRPGQGLEWIGKIGPGSGRTYYNEK<br>FKGKATLTADKSSTAYIQISSLTSEDSAVYFCAVLSWGQGTLVTVSS |
| SEQ ID NO. 20 | DVQITQTPLTLSVTFGQPASISCKSSQSLLKSDGRTYLNWLLQRPGQSPKRLLYLVSKLDSGV<br>PDRFTGSGSGTDFTLKISRVEAEDLGVYYCWQGTHFPQTFGGGTKLEIK |
| SEQ ID NO. 21 | DVQITQTPLTLSVTFGQPASISCKSSQSLLKSDGRTYLNWLLQRPGQSPKRLLYLVSKLDSGV<br>PDRFTGSGSGTDFTLKISRVEAEDLGVYYCWQGTHFPQTFGGGTHLTVL |
| SEQ ID NO. 22 | QSVLTQPASVSGSLGQRVTISCKSSQSLLKSDGRTYLNWLLQRPGQSPKRLLYLVSKLDSGVP<br>DRFTGSGSGTDFTLKISRVEAEDLGVYYCWQGTHFPQTFGGGTHLTVL |
| SEQ ID NO. 23 | QVQLQQSRAELVRPGASVTLSCKPSGYTFTDYEVHWVKQTPVHGLEWIGAIDPETGGTADNQK<br>FKGKAILTADKSSSTAYMELRSLTSEDSAVYYCTNFVDVWGTGTTVTVSS |
| SEQ ID NO. 24 | DVVMSQSPSSLAVSVGEKVTMSCKSSQSLLYSGNQKNYLAWYQQKPGQSPRLLIYWASTRESG<br>VPDRFTGSGSGTDFTLTISSVKAEDLAVFYCQQYYNYPLTFGAGTKLELK |
| SEQ ID NO. 25 | DVVMSQSPSSLAVSVGEKVTMSCKSSQSLLYSGNQKNYLAWYQQKPGQSPRLLIYWASTRESG<br>VPDRFTGSGSGTDFTLTISSVKAEDLAVFYCQQYYNYPLTFGGGTHLTVL |
| SEQ ID NO. 26 | DIVTSQSPSSLAVSVGEKVTMSCKSSQSLLYSSNQKNYLAWYQQKPGQSPKLLIYWASTRESG<br>VPDRFTGSGSGTDFTLTISSVKAEDLAVYYCQQYYNYPLTFGGGTHLTVL |
| SEQ ID NO. 27 | EVQLQQSVAELVRPGASVTLSCKASGYTFTDYEMHWVKQTPVHGLEWIGEIDPETGGTAYNQK<br>FKGKAILTADKSSSTAYMELRSLTSEDSAVYYCTEYAMDYWGQGTLVTVSS |
| SEQ ID NO. 28 | DIVTSQSPSSLAVSVGEKVTMSCKSSQSLLYSSNQKNYLAWYQQKPGQSPKLLIYWASTRESG<br>VPDRFTGSGSGTDFTLTISSVKAEDLAVYYCQQYYNYPLTFGAGTKLELK |
| SEQ ID NO. 29 | EVQLQQSVAELVRPGASVTLSCKASGYTFTDYEMHWVKQTPVHGLEWIGEIDPETGGTAYNQK<br>FKGKAILTADKSSSTAYMELRSLTSEDSAVYYCTEYAMDYWGQGTSVTVSS |
| SEQ ID NO. 30 | RVQLKQSGAELVKPGASVKISCKASGYTFTDYYINWVKQRPGQGLEWIGKIGPRSGSIYYNEK<br>FKGKATLTADKSSSTAYMQLRSLTSEDSAVYFCAVLKWGQGTLVTVSS |
| SEQ ID NO. 31 | QVQLKQSGAELVKPGASVKISCKASGYTFTDYYINWVKQRPGQGLEWIGKIGPRSGSIYYNEK<br>FKGKATLTADKSSSTAYMQLRSLTSEDSAVYFCAVLKWGQGTLVTVSS |
| SEQ ID NO. 32 | DAVMTQIPLTLSVTIGQPASISCKSSQSLLHSDGKTYLNWLLQRPGQSPKRLIYLVSKLDSGV<br>PDRFTGSGSGTDFTLKISRVEAEDLGVYYCWQGTHFPQTFGGGTKLEIK |
| SEQ ID NO. 33 | DAVMTQIPLTLSVTIGQPASISCKSSQSLLHSDGKTYLNWLLQRPGQSPKRLIYLVSKLDSGV<br>PDRFTGSGSGTDFTLKISRVEAEDLGVYYCWQGTHFPQTFGGGTHLTVL |
| SEQ ID NO. 34 | EIQLQQSGAELVRPGASVTLSCKASGYTFTDYEMHWVKQTPVHGLEWIGGIDPETGGTAYNQK<br>FKGKAILTADKSSSTVYMELRSLTSEDSAVYYCTRDYGTSGYWGQGTTLTVSS |
| SEQ ID NO. 35 | EIQLQQSGAELVRPGASVTLSCKASGYTFTDYEMHWVKQTPVHGLEWIGGIDPETGGTAYNQK<br>FKGKAILTADKSSSTVYMELRSLTSEDSAVYYCTRDYGTSGYWGQGTLVTVSS |
| SEQ ID NO. 36 | DVVVTQTPLSLPVSFGDQVSISCRSSQSLANSYGNTYLSWYLHKPGQSPQLLIYGISNRFSGV<br>PDRFSGSGSGTDFTLKISRVEAEDLGVYFCSQSTHVPWTFGGGTKLEIK |
| SEQ ID NO. 37 | DVVVTQTPLSLPVSFGDQVSISCRSSQSLANSYGNTYLSWYLHKPGQSPQLLIYGISNRFSGV<br>PDRFSGSGSGTDFTLKISRVEAEDLGVYFCSQSTHVPWTFGGGTHLTVL |
| SEQ ID NO. 38 | QVQLQQSRAELVRPGASVTLSCKPSGYTFTDYEVHWVKQTPVHGLEWIGAIDPETGGTADNQK<br>FKGKAILTADKSSSTAYMELRSLTSEDSAVYYCTNFVDVWGTGTTVTVSSASTTAPSVFPLAP<br>SCGSQSGSTVALACLVSGYFPEPVTVSWNSGSLTSGVHTFPSVLQSSGLYSLSSMVTVPSSRW<br>PSETFTCNVAHPASKTKVDKPVPKRENGRVPRPPDCPKCPAPEMLGGPSVFIFPPKPKDTLLI<br>ARTPEVTCVVVDLDPEDPEVQISWFVDGKQMQTAKTQPREEQFNGTYRVVSVLPIGHQDWLKG<br>KQFTCKVNNKALPSPIERTISKARGQAHQPSVYVLPPSREELSKNTVSLTCLIKDFFPPDIDV<br>EWQSNGQQEPESKYRTTPPQLDEDGSYFLYSKLSVDKSRWQRGDTFICAVMHEALHNHYTQKS<br>LSHSPGK |
| SEQ ID NO. 39 | DVVMSQSPSSLAVSVGEKVTMSCKSSQSLLYSGNQKNYLAWYQQKPGQSPRLLIYWASTRESG<br>VPDRFTGSGSGTDFTLTISSVKAEDLAVFYCQQYYNYPLTEGGGTHLTVLGQPKASPSVTLFP<br>PSSEELGANKATLVCLISDFYPSGVTVAWKADGSPITQGVETTKPSKQSNNKYAASSYLSLTP<br>DKWKSHSSFSCLVTHEGSTVEKKVAPAECS |

SEQUENCE LISTING

| SEQ ID NO. | Sequence |
|---|---|
| SEQ ID NO. 40 | QVQLKQSGAELVKPGASVKISCKASGYTFTDYYINWVKQRPGQGLEWIGKIGPRSGSIYYNEK FKGKATLTADKSSSTAYMQLRSLTSEDSAVYFCAVLKWGQGTLVTVSSASTTAPSVFPLAPSC GSQSQGSTVALACLVSGYFPEPVTVSWNSGSLTSGVHTFPSVLQSSGLYSLSSMVTVPSSRWPS ETFTCNVAHPASKTKVDKPVPKRENGRVPRPPDCPKCPAPEMLGGPSVFIFPPKPKDTLLIAR TPEVTCVVVDLDPEDPEVQISWFVDGKQMQTAKTQPREEQFNGTYRVVSVLPIGHQDWLKGKQ FTCKVNNKALPSPIERTISKARGQAHQPSVYVLPPSREELSKNTVSLTCLIKDFFPPDIDVEW QSNGQQEPESKYRTTPPQLDEDGSYFLYSKLSVDKSRWQRGDTFICAVMHEALHNHYTQKSLS HSPGK |
| SEQ ID NO. 41 | DAVMTQIPLTLSVTIGQPASISCKSSQSLLHSDGKTYLNWLLQRPGQSPKRLIYLVSKLDSGV PDRFTGSGSGTDFTLKISRVEAEDLGVYYCWQGTHFPQTFGGGTHLTVLGQPKASPSVTLFPP SSEELGANKATLVCLISDFYPSGVTVAWKADGSPITQGVETTKPSKQSNNKYAASSYLSLTPD KWKSHSSFSCLVTHEGSTVEKKVAPAECS |
| SEQ ID NO. 42 | EIQLQQSGAELVRPGASVTLSCKASGYTFTDYEMHWVKQTPVHGLEWIGGIDPETGGTAYNQK FKGKAILTADKSSSTVYMELRSLTSEDSAVYYCTRDYGTSGYWGQGTLVTVSSASTTAPSVFP LAPSCGSQSQGSTVALACLVSGYFPEPVTVSWNSGSLTSGVHTFPSVLQSSGLYSLSSMVTVPS SRWPSETFTCNVAHPASKTKVDKPVPKRENGRVPRPPDCPKCPAPEMLGGPSVFIFPPKPKDT LLIARTPEVTCVVVDLDPEDPEVQISWFVDGKQMQTAKTQPREEQFNGTYRVVSVLPIGHQDW LKGKQFTCKVNNKALPSPIERTISKARGQAHQPSVYVLPPSREELSKNTVSLTCLIKDFFPPD IDVEWQSNGQQEPESKYRTTPPQLDEDGSYFLYSKLSVDKSRWQRGDTFICAVMHEALHNHYT QKSLSHSPGK |
| SEQ ID NO. 43 | DVVVTQTPLSLPVSFGDQVSISCRSSQSLANSYGNTYLSWYLHKPGQSPQLLIYGISNRFSGV PDRFSGSGSGTDFTLKISRVEAEDLGVYFCSQSTHVPWTFGGGTHLTVLGQPKASPSVTLFPP SSEELGANKATLVCLISDFYPSGVTVAWKADGSPITQGVETTKPSKQSNNKYAASSYLSLTPD KWKSHSSFSCLVTHEGSTVEKKVAPAECS |
| SEQ ID NO. 44 | ASTTAPSVFPPLAPSCGTTSGATVALACLVLGYFPEPVTVSWNSGALTSGVHTFPSVLQASGLY SLSSMVTVPSSRWLSDTFTCNVAHPPSNTKVDKTVRKTDHPPGPKPCDCPKCPPPEMLGGPSI FIFPPKPKDTLSISRTPEVTCLVVDLGPDDSDVQITWFVDNTQVYTAKTSPREEQFNSTYRVV SVLPILHQDWLKGKEFKCKVNSKSLPSPIERTISKDKGQPHEPQVYVLPPAQEELSRNKVSVT CLIEGFYPSDIAVEWEITGQPEPENNYRTTPPQLDSDGTYFLYSRLSVDRSRWQRGNTYTCSV SHEALHSHHTQKSLTHSPGK |
| SEQ ID NO. 45 | ASTTAPSVFPPLAPSCGTTSGATVALACLVLGYFPEPVTVSWNSGALTSGVHTFPPAVLQASGLY SLSSMVTVPSSRWLSDTFTCNVAHPPSNTKVDKTVRKTDHPPGPKPCDCPKCPPPEMLGGPSI FIFPPKPKDTLSISRTPEVTCLVVDLGPDDSDVQITWFVDNTQVYTAKTSPREEQFNSTYRVV SVLPILHQDWLKGKEFKCKVNSKSLPSPIERTISKDKGQPHEPQVYVLPPAQEELSRNKVSVT CLIKSFHPPDIAVEWEITGQPEPENNYRTTPPQLDSDGTYFVYSKLSVDRSHWQRGNTYTCSV SHEALHSHHTQKSLTHSPGK |
| SEQ ID NO. 46 | RSDAQPSVFLFQPSLDELHTGSASIVCILNDFYPKEVNVKWKVDGVVQNKGIQESTTEQNSKD STYSLSSTLTMSSTEYQSHEKFSCEVTHKSLASTLVKSFNRSECQRE |

Biological Deposit

| Deposited plasmid | ATCC Designation | Designation herein |
|---|---|---|
| Clone 1L | PTA-121215 | CD20-1 (light chain) |
| Clone 1H | PTA-121216 | CD20-1 (heavy chain) |
| Clone 2L | PTA-121217 | CD20-2 (light chain) |
| Clone 2H | PTA-121218 | CD20-2 (heavy chain) |
| Clone 3L | PTA-121219 | CD20-3 (light chain) |
| Clone 3H | PTA-121220 | CD20-3 (heavy chain) |
| Clone 4L | PTA-121207 | CD20-4 (light chain) |
| Clone 4H | PTA-121208 | CD20-4 (heavy chain) |
| Clone 5L | PTA-121211 | CD20-5 (light chain) |
| Clone 5H | PTA-121210 | CD20-5 (heavy chain) |
| Clone 6L | PTA-121209 | CD20-6 (light chain) |
| Clone 6H | PTA-121206 | CD20-6 (heavy chain) |

The invention claimed is:

1. An antibody or antibody fragment recognizing a canine or feline CD20, wherein said antibody or antibody fragment comprises a light chain comprising a sequence selected from SEQ ID NOs: 24, 25, and 39, and a heavy chain comprising a sequence selected from SEQ ID NOs: 23, and 38.

2. The antibody or antibody fragment according to claim 1 which is a heterochimeric antibody.

3. The antibody or antibody fragment according to claim 1 which binds to canine CD20 and wherein the antibody or antibody fragment comprises a constant region and where the constant region is of canine origin.

4. The antibody or antibody fragment according to claim 1 which binds to feline CD20.

5. The antibody or antibody fragment claim 1 comprising a constant domain, wherein the constant domain comprises a sequence selected for providing enhanced ADCC and/or CDC.

6. The antibody or antibody fragment of claim 1 recognizing a canine or feline CD20, and wherein the heavy chain comprises SEQ ID NO: 23.

7. The antibody or antibody fragment of claim 1 recognizing a canine or feline CD20, and wherein the light chain comprises SEQ ID NO: 24.

8. The antibody or antibody fragment of claim 1 recognizing a canine or feline CD20, and wherein the light chain comprises SEQ ID NO: 25.

9. The antibody or antibody fragment of claim 1 recognizing a canine or feline CD20, and wherein the heavy chain comprises SEQ ID NO: 38.

10. The antibody or antibody fragment of claim 1 recognizing a canine or feline CD20, and wherein the light chain comprises SEQ ID NO: 39.

11. The antibody or antibody fragment of claim 1 recognizing a canine or feline CD20, and wherein the heavy chain comprises SEQ ID NO: 38 and wherein the light chain comprises SEQ ID NO: 39.

* * * * *